(12) United States Patent
Takehara et al.

(10) Patent No.: US 11,534,117 B2
(45) Date of Patent: Dec. 27, 2022

(54) IMAGING TABLE AND MANUFACTURING METHOD THEREFOR, MAMMOGRAPHY APPARATUS IMAGING TABLE AND MANUFACTURING METHOD THEREFOR, AND MAMMOGRAPHY APPARATUS

(71) Applicant: Toray Industries, Inc., Tokyo (JP)

(72) Inventors: Tomohiro Takehara, Ehime (JP);
Mitsushige Hamaguchi, Nagoya (JP);
Masato Honma, Ehime (JP)

(73) Assignee: TORAY INDUSTRIES, INC., Tokyo (JP)

( * ) Notice: Subject to any disclaimer, the term of this patent is extended or adjusted under 35 U.S.C. 154(b) by 9 days.

(21) Appl. No.: 16/982,803

(22) PCT Filed: Mar. 20, 2019

(86) PCT No.: PCT/JP2019/011938
§ 371 (c)(1),
(2) Date: Sep. 21, 2020

(87) PCT Pub. No.: WO2019/182077
PCT Pub. Date: Sep. 26, 2019

(65) Prior Publication Data
US 2021/0030376 A1 Feb. 4, 2021

(30) Foreign Application Priority Data

Mar. 23, 2018 (JP) .............................. JP2018-055837
Mar. 23, 2018 (JP) .............................. JP2018-055838
Mar. 23, 2018 (JP) .............................. JP2018-055839

(51) Int. Cl.
*A61B 6/04* (2006.01)
*A61B 6/00* (2006.01)
*B29C 45/17* (2006.01)

(52) U.S. Cl.
CPC ............ *A61B 6/0435* (2013.01); *A61B 6/502* (2013.01); *B29C 45/17* (2013.01)

(58) Field of Classification Search
CPC ....... A61B 6/04; A61B 6/0407; A61B 6/0414; A61B 6/0442; A61B 6/42; A61B 6/4283;
(Continued)

(56) References Cited

U.S. PATENT DOCUMENTS 5,212,719 A 5/1993 Virta et al.
8,331,536 B2 * 12/2012 Shaw .................... A61B 6/502
378/154

(Continued)

FOREIGN PATENT DOCUMENTS

CN 105415716 A * 3/2016 ............. B29C 70/68
FR 2906617 A1 * 4/2008 ........... A61B 6/4233
(Continued)

OTHER PUBLICATIONS

International Search Report and Written Opinion for International Application No. PCT/JP2019/011938, dated Jun. 18, 2019, with partial English translation, 7 pages.
(Continued)

*Primary Examiner* — Jurie Yun
(74) *Attorney, Agent, or Firm* — RatnerPrestia

(57) ABSTRACT

An imaging table to be supported in a cantilever state on an X-ray imaging apparatus, includes a planar body including an opening portion in a surface to be connected to the apparatus, and a coupling member to be connected to the apparatus. The planar body includes a first member forming a top surface including an X-ray irradiation surface, and a second member forming a bottom surface opposed to the X-ray irradiation surface and a standing wall portion erectly provided on an outer circumference of the bottom surface. The second member is bonded to the first member in the
(Continued)

standing wall portion. The first member and the coupling member are bonded to each other. The first member has an aluminum-equivalent X-ray transmission dose of 0.5 mmAL or less at any point in the X-ray irradiation surface.

9 Claims, 18 Drawing Sheets

(58) Field of Classification Search
CPC ....... A61B 6/44; A61B 6/502; A61B 2560/04; A61B 2560/0406; A61B 2560/06; A61B 2562/16; A61B 2562/17; B29C 45/17; B29C 45/1723
See application file for complete search history.

(56) References Cited

U.S. PATENT DOCUMENTS

| | | | |
|---|---|---|---|
| 2006/0115041 A1 | 6/2006 | Roncaglioni et al. | |
| 2007/0189447 A1* | 8/2007 | Holler | G03B 42/02 378/37 |
| 2013/0303661 A1 | 11/2013 | Oka et al. | |
| 2014/0093034 A1 | 4/2014 | Takata et al. | |
| 2014/0180082 A1 | 6/2014 | Evans et al. | |
| 2015/0164449 A1* | 6/2015 | Ko | A61B 6/502 378/37 |
| 2017/0239895 A1* | 8/2017 | Takehara | B32B 27/12 |
| 2018/0284845 A1 | 10/2018 | Honma et al. | |
| 2019/0002655 A1 | 1/2019 | Takebe et al. | |

FOREIGN PATENT DOCUMENTS

| | | | |
|---|---|---|---|
| JP | 04285541 A | 10/1992 | |
| JP | 2006187501 A | 7/2006 | |
| JP | 2010035622 A | 2/2010 | |
| JP | 2010039267 A | 2/2010 | |
| JP | 2011072667 A | 4/2011 | |
| JP | 2012007945 A | 1/2012 | |
| JP | 2012010963 A | 1/2012 | |
| JP | 2012192122 A | 10/2012 | |
| JP | 2012211310 A | 11/2012 | |
| JP | 2013202294 A | 10/2013 | |
| JP | 2013224949 A | 10/2013 | |
| JP | 2014068885 A | 4/2014 | |
| JP | 2014166263 A | 9/2014 | |
| JP | 2016070890 A | 5/2016 | |
| JP | 2016070890 A * | 5/2016 | ........... A61B 6/4233 |
| WO | 2012102202 A1 | 8/2012 | |
| WO | 2016075648 A1 | 5/2016 | |
| WO | 2017047443 A1 | 3/2017 | |
| WO | 2017110528 A1 | 6/2017 | |

OTHER PUBLICATIONS

JIS Z 4701-1997 "General Rule for Medical X-ray Equipment," (https://kikakurui.com/z4/Z4701-1997-01.html), 23 pages, with partial translation.
Japanese Notice of Opposition for Japanese Application No. 2021-700218, dated Mar. 29, 2021, with translation, 70 pages.
Partial Supplementary European Search Report for European Application No. 19 772 380.2, dated Nov. 19, 2021, 10 pages.
Extended European Search Report for European Application No. 19 772 380.2, dated Feb. 22, 2022, 13 pages.

* cited by examiner

Mammography Apparatus Body Side

Cross Section in y-z Plane

Cross Section in y-z Plane

Cross Section in y-z Plane

Cross Section in x-z Plane

Cross Section in y-z Plane

Cross Section in x-z Plane

Cross Section in y-z Plane

Cross Section in y-z Plane

Mammography Apparatus Body Side

Cross Section in y-z Plane

Cross Section in x-z Plane

Cross Section in y-z Plane

Cross Section in y-z Plane

Cross Section in y-z Plane

Cross Section in y-z Plane

IMAGING TABLE AND MANUFACTURING METHOD THEREFOR, MAMMOGRAPHY APPARATUS IMAGING TABLE AND MANUFACTURING METHOD THEREFOR, AND MAMMOGRAPHY APPARATUS

CROSS REFERENCE TO RELATED APPLICATIONS

This is the U.S. National Phase application of PCT/JP2019/011938, filed Mar. 20, 2019, which claims priority to Japanese Patent Application No. 2018-055837, filed Mar. 23, 2018, Japanese Patent Application No. 2018-055838, filed Mar. 23, 2018 and Japanese Patent Application No. 2018-055839, filed Mar. 23, 2018, the disclosures of each of these applications being incorporated herein by reference in their entireties for all purposes.

FIELD OF THE INVENTION

The present invention relates to an imaging table including a plurality of members, an imaging table for a mammography apparatus including a plurality of members, and a method for manufacturing the same.

BACKGROUND OF THE INVENTION

A common mammography apparatus obtains image data by X-ray imaging of a breast of an examinee in order to examine the breast (Patent Literature 1). The mammography apparatus is provided with an imaging table and a pressing plate for pressing the breast in order to obtain image data high in contrast or resolution with little geometric blur or defocusing caused by body motion. The breast supported on the imaging table is pressed by the pressing plate to be retained at a uniform thickness, and then the breast is irradiated with X-rays, and the X-rays transmitted by the breast are detected to generate image data.

The imaging table is internally provided with an X-ray detection portion for detecting X-rays penetrating the pressing plate and a breast as a subject to be imaged. Therefore, the imaging table is formed by a material excellent in X-ray transparency. In addition, the subject is pressed so as to have uniform thickness by the pressing plate during imaging. Accordingly, an external force caused by the pressing plate also acts on the imaging table. In the case where the imaging table is easily deformed by the external force, obtained image data may deteriorate in contrast or resolution. Therefore, it is typically necessary to form the imaging table by a material excellent in rigidity. From the aforementioned background, a carbon fiber reinforced composite material (carbon composite material) excellent in X-ray transparency and high in rigidity is used suitably for an imaging table for a mammography apparatus as described in Patent Literature 1. Since an imaging table for a mammography apparatus has a complicated shape, that is, typically a hollow box-like shape as a generally commercially available product, a manufacturing method is used as follows in the case of using such a carbon fiber reinforced composite material. That is, a carbon fiber woven fabric prepreg excellent in shape followability is disposed on a surface of a single-surface mold to impart the shape of the mold to the prepreg, and the prepreg is heated and pressed by an autoclave.

For mammography, besides the aforementioned imaging method using the imaging table, another method for directly imaging a subject placed on a cassette is also disclosed (Patent Literature 2). Since this imaging method uses a thin and rectangular cassette, the imaging method can avoid an increase in weight, and thus the handleability can be improved. The medical cassette according to Patent Literature 2 is constituted by a front member and a back member opposed to the front member so that an image recording medium can be received inside the cassette. It is also suggested that the front member and the back member can be separated from each other. In addition, the front member to be irradiated with X-rays is integrated with an outer circumferential frame member. Thus, there is an effect that deformation during imaging can be inhibited. Here Patent Literature 2 suggests that the front member is constituted by a laminate which is obtained by a plurality of layers (carbon fiber layers) each having a large number of carbon fiber filaments are arrayed in one direction are put on top of one another and impregnated with a thermosetting resin. In addition, as a manufacturing method thereof, a method for manufacturing by an RTM (Resin Transfer Molding) method in which the carbon fiber filaments are laid in a mold and the resin is injected into a cavity is disclosed.

PATENT LITERATURE

Patent Literature 1: JP-A-2010-35622
Patent Literature 2: JP-A-2010-39267

SUMMARY OF THE INVENTION

However, the imaging table for a mammography apparatus generally commercially available as a product has a hollow box-like shape. Accordingly, even in the case where the carbon fiber woven fabric prepreg excellent in shape followability is used, it is necessary to cut the prepreg in a cut pattern corresponding to the shape of the imaging table and shape by the single-surface mold in order to follow corner portions or curved faces. Thus, the process may be complicated. In addition, a single prepreg base material is cut out into various shapes. Thus, the yield of the base material may deteriorate to increase the raw material cost. From the above background, there is a problem in improvement of productivity.

On the other hand, in the invention according to Patent Literature 2, the medical cassette has a thin and rectangular shape to receive the image recording medium inside the cassette as described above. It is therefore natural to take a configuration in which the front member and the back member can be separated from each other. Under the imaging conditions where the cassette is put under a body of an examinee as in roentgenography, the resin frame can receive a load to secure rigidity. However, if the configuration is applied as it is to the imaging conditions where a load acts on the center through the pressing plate as in the imaging table for a mammography apparatus, a front panel forming a flat face portion may be bent easily at the center thereof. In addition, since the medical cassette has a thin and rectangular shape, in the case where the cassette is supported in a cantilever state and used as the imaging table, the medical cassette is deformed easily as a whole due to the load applied from the pressing plate. Thus, the contrast or resolution of obtained image data may deteriorate. Further, there is a fear that a standing wall portion biting the examinee may give a feeling of discomfort to the examinee during imaging by mammography. In addition, the RTM method disclosed as the manufacturing method has a lot of limitations. For example, the resin is limited to be liquid in order to be injected and impregnated into a fiber base material. It is therefore difficult to shorten the molding time satisfactorily. Further, both the autoclave method and the RTM method require a secondary material for molding. Thus, there is a problem that the manufacturing cost increases.

Therefore, the present invention has been developed in consideration of the aforementioned problems. An object of the invention is to provide an imaging table, and an imaging table for a mammography apparatus, capable of achieving high X-ray transparency and high rigidity and capable of achieving a high degree of freedom in shape with good productivity. Another object of the invention is to provide a method for manufacturing an imaging table for a mammography apparatus with good productivity and in a short molding time.

In order to solve the problem, the imaging table in exemplary embodiments of the present invention has the following configuration:

an imaging table to be supported in a cantilever state on an X-ray imaging apparatus, the imaging table including a planar body including an opening portion in a surface to be connected to the apparatus, and a coupling member to be connected to the apparatus, in which:

the planar body includes a first member forming a top surface including an X-ray irradiation surface, and a second member forming a bottom surface opposed to the X-ray irradiation surface and a standing wall portion erectly provided on an outer circumference of the bottom surface;

the second member is bonded to the first member in the standing wall portion;

the first member and the coupling member are bonded to each other; and the first member has an aluminum-equivalent X-ray transmission dose of 0.5 mmAL or less at any point in the X-ray irradiation surface.

Further, a method for manufacturing an imaging table in exemplary embodiments of the present invention is as follows:

a method for manufacturing an imaging table to be supported in a cantilever state on an X-ray imaging apparatus, the imaging table including a planar body including an opening portion connected to the X-ray imaging apparatus, the planar body including a first member forming a top surface including an X-ray irradiation surface, a second member forming a bottom surface opposed to the X-ray irradiation surface, and a third member reinforcing the first member, the method for manufacturing an imaging table including the following steps (I) to (III):

Step (I): heating and pressurizing a preform including a prepreg laminate including continuous fibers (A) and a matrix resin (B) in female and male double-surface molds, thereby molding the first member to form the top surface including the X-ray irradiation surface by a fiber composite material;

Step (II): integrating the second member with at least the first member; and

Step (III): integrating the third member with at least the first member.

Further, an imaging table for mammography apparatus in exemplary embodiments of the present invention has the following configuration:

an imaging table for a mammography apparatus to be supported in a cantilever state on the mammography apparatus, the imaging table including:

a first member forming a top surface including an X-ray irradiation surface; and a second member forming a bottom surface opposed to the X-ray irradiation surface and a standing wall portion erectly provided on an outer circumference of the bottom surface, in which the second member is bonded to the first member in the standing wall portion; and in which the first member has an aluminum-equivalent X-ray transmission dose of 0.5 mmAL or less at any point in the X-ray irradiation surface.

Further, a method for manufacturing an imaging table for a mammography apparatus in exemplary embodiments of the present invention is as follows:

a method for manufacturing an imaging table for a mammography apparatus to be supported in a cantilever state on the mammography apparatus, the imaging table for a mammography apparatus including a first member to form a top surface including an X-ray irradiation surface, a second member to form a bottom surface opposed to the X-ray irradiation surface, and a third member to reinforce the first member, the method for manufacturing an imaging table for a mammography apparatus including the following steps (I) to (III):

Step (I): heating and pressurizing a preform including a prepreg laminate including continuous fibers (A) and a matrix resin (B) in female and male double-surface molds, thereby molding the first member forming the top surface including the X-ray irradiation surface by a fiber composite material;

Step (II): integrating the second member with at least the first member; and

Step (III): integrating the third member with at least the first member.

In an imaging table or an imaging table for a mammography apparatus according to embodiments of the present invention, the number of complicated shapes such as corner portions or curved faces in individual members can be reduced to simplify processing steps and attain good productivity. In addition, due to a configuration including a first member having X-ray transparency and a second member forming an outer plate shape, a function of securing X-ray transparency and rigidity and a function of imparting a shape of a handle for an examinee or the like can be separated. Thus, it is possible to provide an imaging table for a mammography apparatus retaining functions usually required for imaging by mammography while making it easy to design the complicated shapes with good productivity. In addition, the mechanical characteristic of a bonding portion is high in spite of the two-split structure. Thus, it is possible to provide an imaging table for a mammography apparatus capable of inhibiting the imaging table from bending due to a load applied during imaging by mammography, so as to improve the quality of a taken image.

In a method for manufacturing an imaging table for a mammography apparatus, the number of complicated shapes such as corner portions or curved faces can be reduced to simplify a step of cutting a base material or a step of lamination. Thus, it is possible to manufacture the imaging table for a mammography apparatus in a short forming time and with good productivity.

BRIEF DESCRIPTION OF DRAWINGS

FIG. 2c is a sectional view showing an example of a sectional shape taken on y-z plane in FIG. 2a.

FIG. 3c is a sectional view showing an example of a sectional shape taken on y-z plane in FIG. 3a.

FIG. 4b is a sectional view showing an example of a sectional shape taken on y-z plane in FIG. 4a.

FIG. 5b is a sectional view showing an example of a sectional shape taken on x-z plane in FIG. 5a.

FIG. 5c is a sectional view showing an example of a sectional shape taken on y-z plane in FIG. 5a.

FIG. 7b is a sectional view showing an example of a sectional shape taken on x-z plane in FIG. 7a.

FIG. 7c is a sectional view showing an example of a sectional shape taken on y-z plane in FIG. 7a.

FIG. 10c is a sectional view showing an example of a sectional shape taken on y-z plane in FIG. 10a.

FIG. 11c is a sectional view showing an example of a sectional shape taken on y-z plane in FIG. 11a.

FIG. 13b is a sectional view showing an example of the sectional shape taken on x-z plane in FIG. 13a.

FIG. 13c is a sectional view showing an example of the sectional shape taken on y-z plane in FIG. 13a.

FIG. 17 is a sectional view showing an example of the sectional shape on y-z plane in FIG. 2a.

FIG. 18a is a sectional view showing an example of the sectional shape on y-z plane in FIG. 2a.

FIG. 18b is a sectional view showing an example of the sectional shape on y-z plane in FIG. 2a.

DETAILED DESCRIPTION OF EMBODIMENTS OF THE INVENTION

Figure 1:
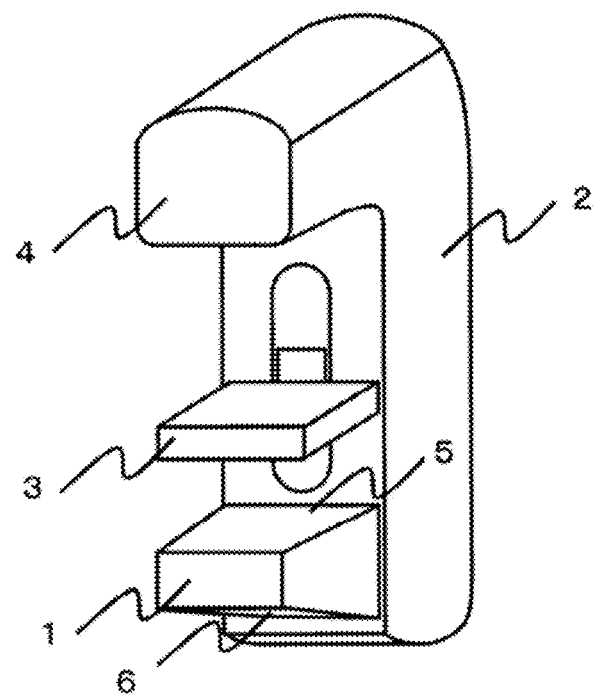
FIG. 1 is a block diagram showing a configuration of a mammography apparatus according to an embodiment of the present invention.

An imaging table according to an embodiment of the present invention is an imaging table supported in a cantilever state on an X-ray imaging apparatus, and includes a configuration as follows. The imaging table includes a planar body including an opening portion in a surface to be connected to the X-ray imaging apparatus, and a coupling member to be connected to the X-ray imaging apparatus. The planar body includes a first member forming a top surface including an X-ray irradiation surface, and a second member forming a bottom surface opposed to the X-ray irradiation surface, and a standing wall portion erectly provided on an outer circumference of the bottom surface. The second member is bonded to the first member in the standing wall portion. The first member and the coupling member are bonded to each other. The first member has an aluminum-equivalent X-ray transmission dose of 0.5 mmAL or less at any point in the X-ray irradiation surface. The application of the imaging table is not limited as long as it is supported in a cantilever state on an X-ray imaging apparatus. For example, the imaging table is an imaging table for a mammography apparatus.

The mammography apparatus according to the embodiment of the present invention is formed by connecting the imaging table for a mammography apparatus to a body of the mammography apparatus. The imaging table for a mammography apparatus according to embodiments of the present invention will be described below.

The aluminum-equivalent X-ray transmission dose at any point in the X-ray irradiation surface of the first member may be 0.5 mmAL or less in any condition of an X-ray irradiation tube voltage, or may be 0.5 mmAL or less on any condition of the X-ray irradiation tube voltage within a range of 20 kV to 60 kV, or may be 0.5 mmAL or less at the X-ray irradiation tube voltage of 20 kV or 60 kV.

In the imaging table for a mammography apparatus according to the embodiment of the present invention, the material of the first member is not particularly limited as long as the first member forms the top surface including the X-ray irradiation surface and the aluminum-equivalent X-ray transmission dose as an index of X-ray transparency is 0.5 mmAL or less. A fiber-reinforced composite material composed of reinforcing fibers and a matrix resin is preferred in order to achieve high X-ray transparency and inhibit deflection caused by a load applied during imaging. In the case where the aluminum-equivalent X-ray transmission dose (aluminum equivalent) exceeds 0.5 mmAL, the X-ray transparency is worse, causing necessity to increase the X-ray irradiation intensity. Thus, there is a fear that the dose of an examinee exposed during one operation of imaging may increase. On the other hand, the second member includes the bottom surface opposed to the X-ray irradiation surface, and the standing wall portion erectly provided on the outer circumference of the bottom surface. The second member is bonded to the first member in the standing wall portion. The material of the second member is not particularly limited as long as the standing wall portion is formed. However, the second member is preferably made of at least one kind selected from the group consisting of metal, plastic and elastomer in terms of formability to impart a shape such as a handle for the examinee. With such a configuration, the number of curved faces or corner portions can be reduced so that an imaging table having a hollow box-like shape can be manufactured with good productivity. The imaging table according to embodiments of the present invention may additionally include third and fourth members.

The body of the mammography apparatus includes an X-ray generation portion and a pressing plate, and the arrangement thereof is exemplified as illustrated in FIG. 1. The imaging table for a mammography apparatus according to the embodiment of the present invention is supported in a cantilever-like state on the body of the mammography apparatus. In addition, the mammography apparatus shown in FIG. 1 includes a mammography apparatus body 2, a mammography apparatus imaging table 1, a pressing plate 3, and an X-ray generation portion 4. The mammography apparatus imaging table 1 includes an X-ray irradiation surface 5 and a bottom surface 6. In addition, the imaging table for a mammography apparatus according to the embodiment of the present invention typically has an approximately box-like shape with a cavity in its inside. An X-ray detector is often provided inside the cavity. The X-ray detector may be connected to the body of the mammography apparatus directly or may be fixed into the imaging table and connected to the body of the mammography apparatus through wiring. In addition, the X-ray irradiation surface is a flat face region included in the top surface of the imaging table according to the embodiment of the present invention. The flat face region may be the whole of the top surface of the imaging table or may be a part thereof.

A form of the reinforcing fibers in the fiber-reinforced composite material is preferably at least one kind selected from a woven fabric form in which a woven texture is formed by continuous fibers, a form in which continuous fibers are aligned in one direction, a form in which discontinuous fibers are arrayed in one direction, a form in which discontinuous fibers are dispersed, etc. One of those forms used alone or in lamination, or a lamination of two or more kinds of those forms is preferably used. The continuous fibers are fibers which are set up in a continuous state as a reinforcing fiber bundle without being cut off into a short fiber. Here, a short fiber designates a fiber having a length of 100 mm or shorter. In embodiments of the present invention, the reinforcing fibers preferably have a form of continuous fibers in order to gain a uniform in-plane distribution of the X-ray transparency, that is, in order to reduce a variation in the density in the plane. Among the forms, it is preferable to use the form in which continuous fibers are aligned in one direction because the continuous fibers can be arranged without any gap. In addition, the continuous fibers are not particularly limited. Examples of the continuous fibers include glass fibers, polyacrylonitrile (PAN) based fibers, pitch based carbon fibers (including graphite fibers), organic fibers such as aramid, etc. Two or more kinds of those fibers may be used in combination.

The unidirectional fiber composite material having the form in which the continuous fibers are aligned in one direction includes layers each including the continuous fibers aligned in one direction, and a matrix resin. The unidirectional fiber composite material may be constituted by a single layer or may be constituted by a laminate in which two or more layers are laminated. In addition, in the case where two or more layers including carbon fibers aligned in one direction and a matrix resin are laminated, the unidirectional fiber composite material may have a configuration in which orientation directions of the continuous fibers are shifted among the layers desirably. In a preferred lamination configuration, the orientation directions of the carbon fibers are shifted in terms of the yield with which the material is cut out from a sheet-like base material. In addition, in a preferred lamination configuration in view of isotropy, the orientation directions of the carbon fibers are shifted by 30° to 60°. For example, in a preferred lamination configuration, each of the orientation directions of the continuous fibers is shifted by 45°, or each of the orientation directions of the continuous fibers is shifted by 60°.

The woven fabric composite material having a woven fabric form in which a woven texture is formed by the continuous fibers includes a sheet-like woven fabric in which the continuous fibers are woven, and a matrix resin. The woven fabric composite material typically includes a layer structure, which may be constituted by a single layer or may be constituted by a laminate in which two or more layers are laminated. Examples of the woven texture of the continuous fibers include a plain weave, a twill weave, a satin weave, etc. Among them, the twill weave is preferred in terms of shape followability and X-ray transparency.

Further preferably, the woven fabric composite material is contained in the outermost layer of the first member. In the case where the outermost surface to touch a bare skin of an examinee has such a configuration, the continuous fibers can be prevented from fluffing even when the resin deteriorates due to a change with time, for example caused by exposure to an antiseptic solution in an operating environment, as compared with the unidirectional fiber composite material. Thus, a stimulus to the examinee can be relaxed. From this point of view, particularly it is preferable that the outermost layer of the X-ray irradiation surface is formed by the woven fabric composite material, and the unidirectional fiber composite material is disposed in inner layers.

The material of the first member in the present invention preferably contains carbon fiber composite material, in terms of X-ray transparency and high rigidity. The carbon fiber is not particularly limited, but examples of the carbon fiber include polyacrylonitrile (PAN) based fibers, pitch based carbon fibers, etc. A single kind of those fibers may be used, or two or more kinds of them may be used together. Among them, the PAN based carbon fibers are more preferable in terms of balance between strength and elasticity in the carbon fiber composite material obtained therefrom. The strand elastic modulus of the carbon fibers is preferably 200 GPa or more, more preferably 220 GPa or more, and even more preferably 240 GPa or more. In the case where the strand elastic modulus of the carbon fibers is below 200 GPa, intended properties may not be obtained in the carbon fiber composite material obtained therefrom.

The matrix resin is not particularly limited, but either a thermosetting resin or a thermoplastic resin may be used. In the case where the matrix resin is a thermosetting resin, the thermosetting resin is cured to serve as the matrix resin due to heating during molding and, if necessary, due to further heating after the molding to a temperature high enough to cure the thermosetting resin. In the case where the resin is a thermoplastic resin, the resin melted by heating during molding is cooled and solidified to serve as the matrix resin. Examples of the thermosetting resin include epoxy resin, vinyl ester resin, phenolic resin, unsaturated polyester resin, etc. Any thermosetting resin may be used as long as it can cause a crosslinking reaction due to heat to form a three-dimensional crosslinked structure at least partially. On the other hand, a prepreg can be used as a molding base material for forming the carbon fiber composite material. As a form of the thermosetting resin in the prepreg, the thermosetting resin is preferably in a semi-cured state excellent in tackiness so that the prepreg can be bonded in a pressed manner to another prepreg or to a mold when the prepreg is laminated. Among the thermosetting resins, the epoxy resin is preferred in consideration of the tackiness in a pasting step and the mechanical characteristic as a molded product obtained therefrom. Preferred examples of the thermoplastic resin include polypropylene resin, polyethylene resin, polyamide resin, polyester resin, polyarylene sulfide resin, polyphenylene sulfide resin, polyether ketone resin, polyether ether ketone resin, polyether ketone ketone resin, polyether sulfone resin, polyimide resin, polyamide imide resin, polyether imide resin, and polysulfone resin. In addition, a cyclic oligomer which is a precursor of any one of those resins is also used preferably. Among them, a resin excellent in chemical resistance is preferably selected in consideration of cleaning with an antiseptic from the viewpoint of operation of the imaging stand for a mammography apparatus.

In the imaging table in the present invention, the first member has preferably a specific bending elastic modulus of 2.50 or higher. The specific bending elastic modulus is expressed as $Eb^{1/3} \times \rho^{-1}$ where Eb designates the bending elastic modulus and $\rho$ designates the density. In the case where the specific bending elastic modulus of the first member is 2.50 or higher, the bending elastic modulus is relatively high and the density is relatively low. This state is preferable because balance between difficulty in deformation and high X-ray transparency can be kept good. On the other hand, the upper limit of the specific bending elastic modulus is not particularly limited. The specific bending elastic modulus is preferably set at 20.00 or less, because the balance between the effect of improving the X-ray transparency and the bending elastic modulus is excellent.

The material of the second member may be the same as the material of the first member. From the viewpoint of processability and dimensional accuracy, metal is preferably used as the material of the second member. Examples of kinds of the metal include aluminum, copper, nickel, tin, iron, magnesium, chrome, tungsten, zinc, lead, and alloys of those metals. In addition, the second member may be composed of one kind of metal material, or two or more kinds of metals may be combined.

Plastic is preferably used as the material of the second member in terms of moldability/processability and manufacturing cost. Thermosetting resin or thermoplastic resin may be used. Examples of the thermosetting resin include epoxy resin, vinyl ester resin, phenolic resin, polyurethane resin, urea resin, melamine resin, etc. Examples of the thermoplastic resin include propylene resin, polyethylene resin, polycarbonate resin, polyamide resin, polyester resin, polyarylene sulfide resin, and polyphenylene sulfide resin. In addition, a cyclic oligomer which is a precursor of any one of those resins is also used preferably. The plastic as the material of the second member may contain a filler such as glass fibers in order to enhance the mechanical characteristic.

Alternatively, elastomer may be used as the material of the second member in order to protect an examinee. Examples of the elastomer include silicone rubber, urethane rubber, thermoplastic elastomer, etc.

The second member in the present invention can be manufactured by a common molding method such as press molding, injection molding, injection compression molding, compression molding, vacuum molding, extrusion molding, sheeting, or casting.

The imaging table for a mammography apparatus in the present invention preferably has a structure in which the imaging table for a mammography apparatus according to the embodiment of the invention has a surface to be connected to the body of the mammography apparatus, and an opening portion is provided in the connection surface.

Figure 2A:
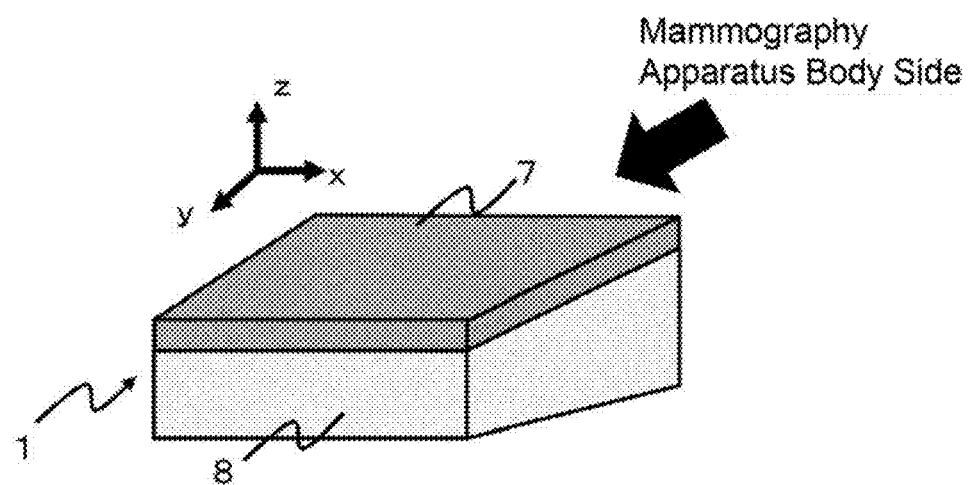
FIG. 2a is a schematic view showing an example of the external appearance of an imaging table for the mammography apparatus according to the embodiment of the present invention.
Figure 2B:
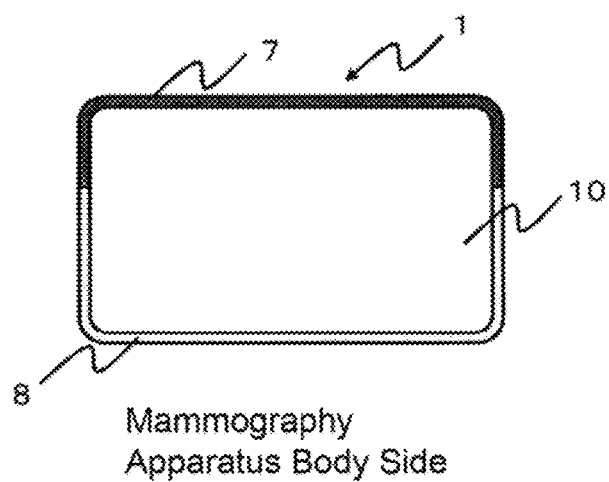
FIG. 2b is a schematic view showing an example of an opening portion of the imaging table for a mammography apparatus according to the embodiment of the present invention.
Figure 2C:
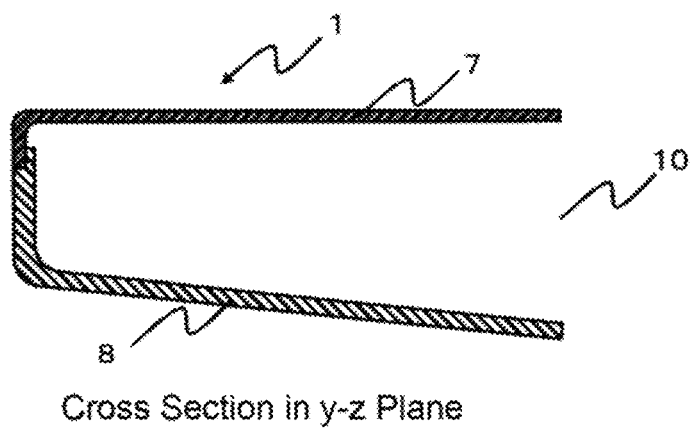
Figure 3A:
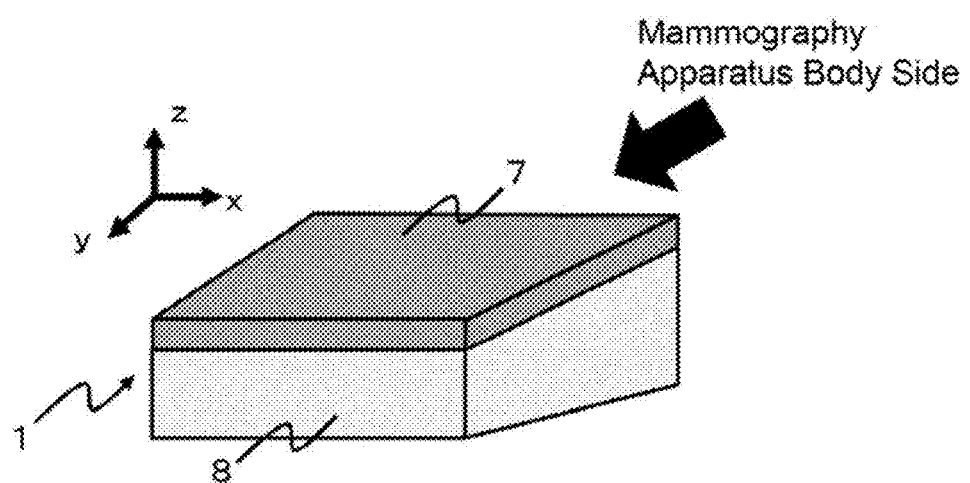
FIG. 3a is a schematic view showing an example of the external appearance of the imaging table for a mammography apparatus according to the embodiment of the present invention.
Figure 3B:
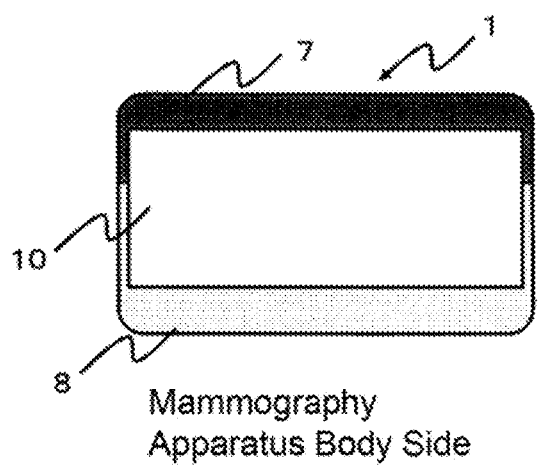
FIG. 3b is a schematic view showing an example of the opening portion of the imaging table for a mammography apparatus according to the embodiment of the present invention.
Figure 3C:
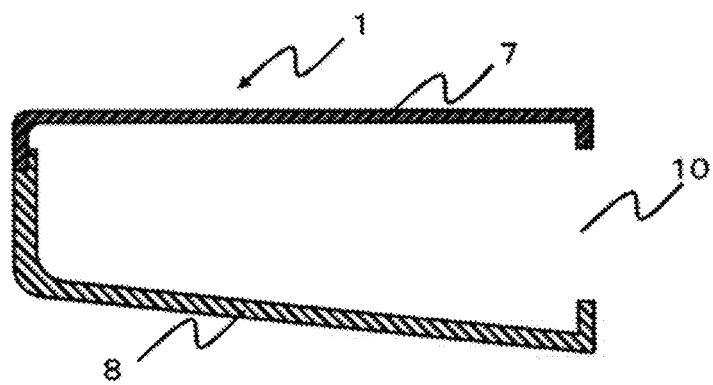

The second member of the imaging table for a mammography apparatus shown in FIG. 2a and FIG. 3a includes a standing wall portion, and an opening portion provided in a connection surface (on the mammography apparatus body side) to be connected to the body of the mammography apparatus. As shown in FIG. 2b and FIG. 2c, the opening portion 10 may be opened all over the connection surface to be connected to the body of the mammography apparatus. Alternatively, as shown in FIG. 3b and FIG. 3c, the opening portion 10 may be opened in a part of the connection surface. FIG. 2c is a sectional view showing an example of a sectional shape taken on y-z plane in the imaging table for a mammography apparatus shown in FIG. 2a. FIG. 3c is a sectional view showing an example of a sectional shape taken on y-z plane in the imaging table for a mammography apparatus shown in FIG. 3*a*.

Due to the opening portion 10 provided in the imaging table for a mammography apparatus, the imaging table for a mammography apparatus can be detached from and attached to the body of the mammography apparatus easily. Thus, maintenance can be performed easily. The height of the standing wall in the imaging table is preferably 10 mm or more. The height of the standing wall is preferably 10 mm or more in the imaging table for a mammography apparatus since it is possible to secure a large space where an X-ray detector can be received. The height of the standing wall is a distance between the upper portion of the top surface of the first member and the top end portion of the standing wall. Further, the height of the standing wall is preferably 20 mm or more, and particularly preferably 30 mm or more.

In the imaging table according to the embodiment of the present invention, the first member has a standing wall portion which is preferably formed to stand on the outer circumference of the top surface. By virtue of the standing wall portion provided in the first member, the deformation caused by a pressure from the pressing plate during imaging by mammography can be prevented. In addition, by virtue of the standing wall provided in each of the first member and the second member, the space where the X-ray detector to be received inside the imaging table can be disposed can be expanded, and the surface to touch an examinee during imaging by mammography can be also secured with a large area. It is therefore possible to inhibit an interference such as bite into a body of the examinee.

Figure 16:
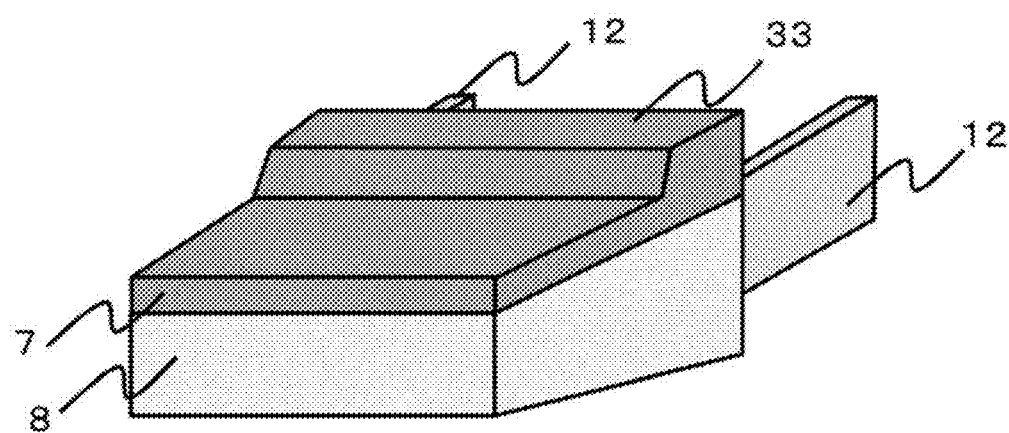
FIG. 16 is a schematic view showing an example of the appearance of the imaging table for a mammography apparatus according to the embodiment of the present invention.

More preferably, a step portion may be provided in a top surface region other than the X-ray irradiation surface in the first member. In the case where such a shape is provided, the step portion functions as a standing wall so that deflection caused by a pressure from the pressing plate during imaging by mammography can be prevented. In addition, the region where the detector etc. can be received inside the imaging table can be expanded. The position where the step portion is provided may be the connection surface to the apparatus by way of example (FIG. 16).

Figure 4A:
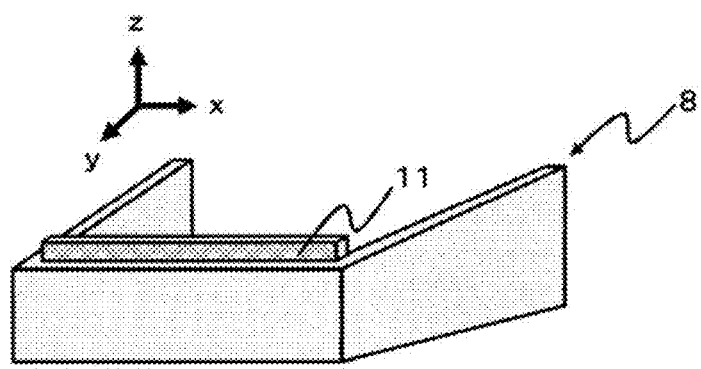
FIG. 4a is a schematic view showing an example of a region (A1) which is provided in an embodiment of a standing wall portion of a second member in the imaging table for a mammography apparatus according to the embodiment of the present invention, so that the standing wall portion of the second member is superimposed on and bonded to a standing wall portion of a first member in the region (A1).
Figure 4B:

More preferably, in order to inhibit deformation of a side surface with a load applied to the imaging table, the standing wall portion of the first member and the standing wall portion of the second member may be bonded to each other. As for the bonding structure between the first member and the second member, an end face of the standing wall of each of the members may be bonded to each other, or not the end faces but the standing wall portion of each of the members may be superimposed on and bonded to each other. A structure (FIG. 4*a*) where the standing wall portion of the second member has a region (A1) superimposed on and bonded to the standing wall portion of the first member is a more preferable bonding structure. By virtue of the structure including the region (A1), the bonding area of each of the members can be expanded so that the members can be bonded more firmly. Thus, the positional accuracy during imaging can be improved to obtain a mammography image with higher resolution.

Figure 17:
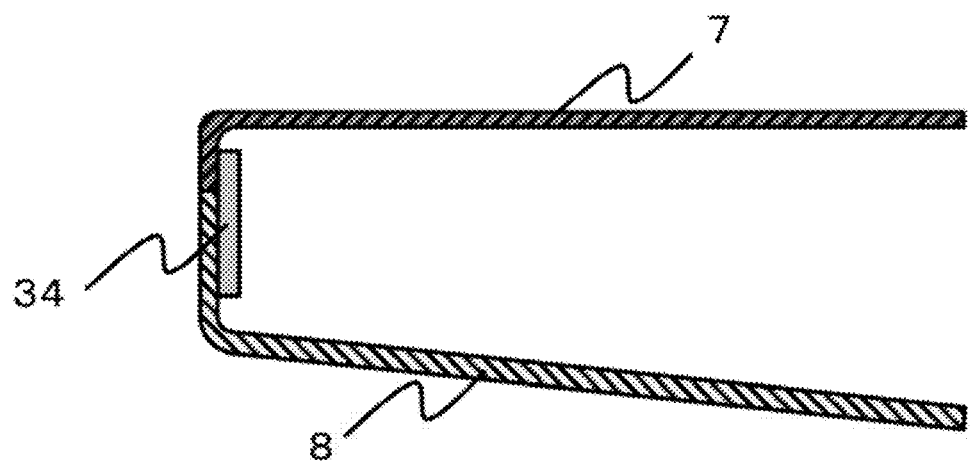

Preferably a third member bonded to both the standing wall portion of the first member and the standing wall portion of the second member may be provided. The third member may be bonded to the inner wall side of the surface an examinee should touch, by way of example (FIG. 17). In such a form, the third member can serve as a reinforcing member, thereby improving the rigidity. Thus, opening can be inhibited from occurring at an end portion of the standing wall portion of the first member and an end portion of the standing wall portion of the second member so that the positional accuracy during imaging can be improved.

Figure 18A:
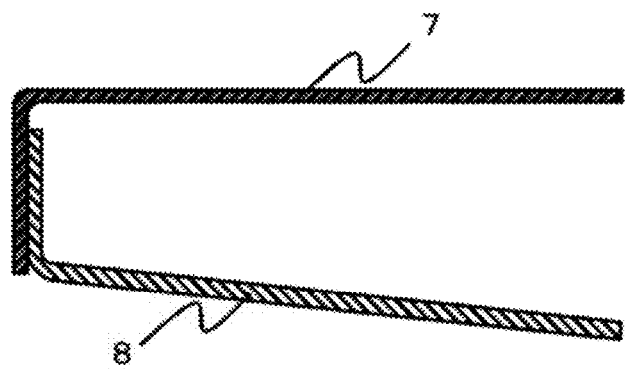
Figure 18B:
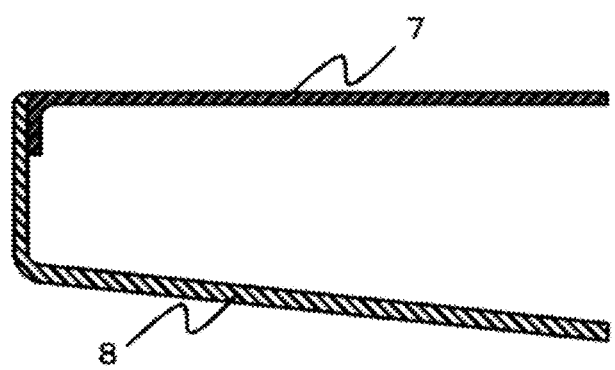

It is preferable that no border line exists between the first member and the second member in an opposed surface to the connection surface to the apparatus. The opposed surface is a surface to be touched by an examinee. In such a form, there is no irregularity in the region the bare skin of the examinee should touch during imaging. It is therefore possible to relax the feeling of discomfort given to the examinee during imaging. The form is not particularly limited as long as no border line exists between the first member and the second member in the opposed surface to the connection surface to the apparatus. Examples of the form include a form (FIG. 18*a*) in which the length of the standing wall located in the opposed surface to the connection surface to the apparatus in the first member is extended to the height of the standing wall of the second member so that the standing walls can be bonded to cover the standing wall of the second member with the standing wall of the first member, and a form (FIG. 18*b*) in which the length of the standing wall located in the opposed surface to the connection surface to the apparatus in the second member is extended to the height of the standing wall of the first member so that the standing walls can be bonded to cover the standing wall of the first member with the standing wall of the second member.

Preferably the imaging table according to the embodiment of the present invention includes a coupling member to be connected to the body of the mammography apparatus, and the coupling member is bonded to the first member. Since the first member receiving a load from the pressing plate during imaging by mammography can be connected to a coupling member of the body of the mammography apparatus through the coupling member of the imaging table, the load can be transmitted to the body of the mammography apparatus which is rigid. Thus, the deformation of the first member can be inhibited to improve the positional accuracy during imaging, thereby obtaining a mammography image with high resolution.

More preferably the coupling member according to the embodiment of the present invention is bonded to both the first member and the second member. In such a bonding form, the mechanical characteristic of the bonding portion can be improved to inhibit the deformation and opening in the side face of the imaging table caused by the load applied during imaging by mammography. Thus, the positional accuracy during imaging can be improved to obtain a mammography image with high resolution.

Figure 7A:
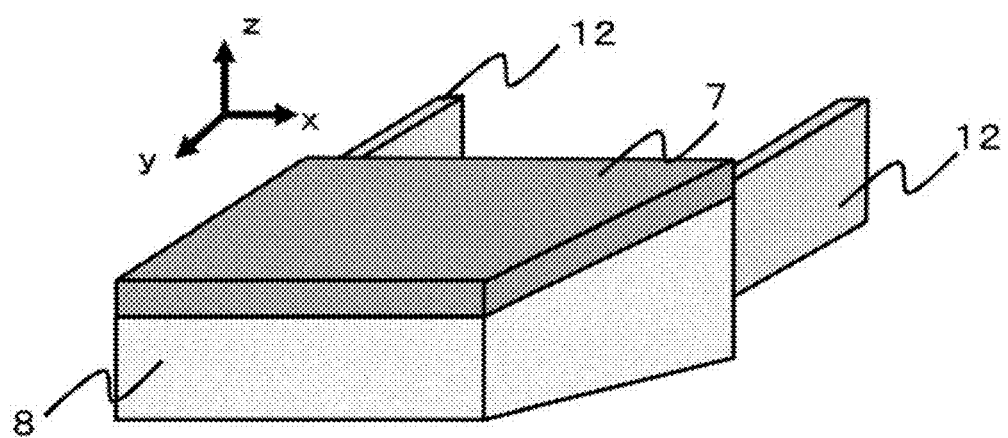
FIG. 7a is a schematic view showing an example of the external appearance of the imaging table for a mammography apparatus according to the embodiment of the present invention.
Figure 7B:
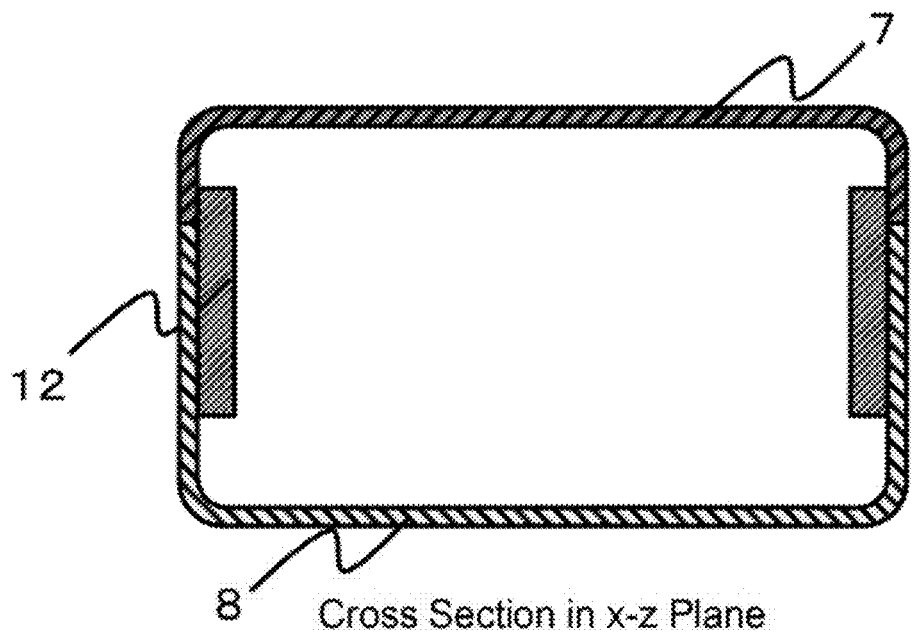
Figure 7C:
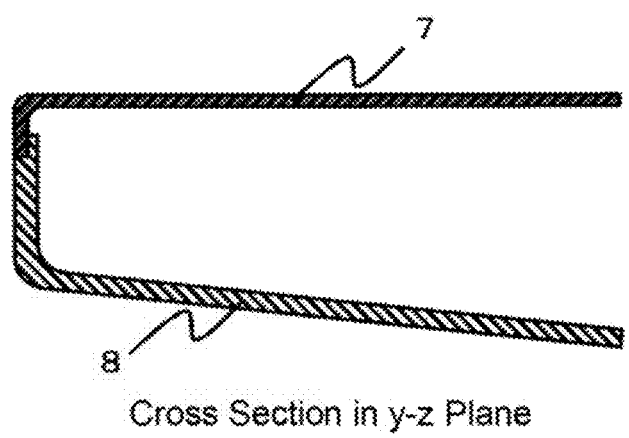

The position where the coupling member is bonded is not particularly limited as long as the coupling member is bonded to the first member. In terms of designability of the obtained imaging table for the mammography apparatus, the coupling member is preferably bonded to the inner wall of the first member, more preferably the inner wall of each of the two side faces in the surface provided with an opening portion which will be described later. In the case where the coupling member is bonded to the side face, the X-ray irradiation surface can be expanded so that even a position close to a body of an examinee subjected to mammography can be imaged. Thus, an area which can be examined can be expanded. In order to improve the mechanical characteristic of the bonded region, the position is preferably a position where the coupling member can be bonded to both the standing wall portion of the first member and the standing wall portion of the second member (FIG. 7*a*, FIG. 7*b* and FIG. 7*c*). In such a configuration, deformation and opening in each side face of the imaging table caused by the load applied during imaging by mammography can be inhibited to improve the positional accuracy during the imaging. Thus, a mammography image can be obtained with high resolution. Examples of the structure for connecting the body of the mammography apparatus and the first member include a method in which the first member is connected to a frame provided in the body of the mammography apparatus via a coupling member bonded to the first member, and a method in which the first member is bonded to a frame-like coupling member, and the coupling member is fixed to the mammography apparatus to connect the first member thereto.

Preferably in the embodiment of the present invention, bonding strength (S1) between the first member and the coupling member is 10 MPa or more. In the case where the bonding strength (S1) is set at 10 MPa or more, the load applied to the first member from the pressing plate during imaging by mammography can be transmitted to the rigid body of the apparatus efficiently, so that deflection of the X-ray irradiation surface in the first member can be inhibited suitably. The bonding strength (S1) is more preferably 15 MPa or more, and particularly preferably 20 MPa or more. Further preferably, bonding strength (S2) between the second member and the coupling member is 10 MPa or more. In the case where the bonding strength (S2) is set at 10 MPa or more, opening in the side face of the imaging table caused by the load applied during imaging by mammography can be inhibited suitably. The bonding strength (S2) is more preferably 15 MPa or more, and particularly preferably 20 MPa or more. The upper limits of the bonding strength (S1) and the bonding strength (S2) are not particularly limited. Preferably the bonding strengths are equivalent to the breaking strength of the base material where the first member and the second member are broken.

Preferably in the embodiment of the present invention, bonding strength (S3) between the first member and the second member is 10 MPa or more. In the case where the bonding strength is set at 10 MPa or more, opening in the bonding portion caused by the load applied during imaging by mammography can be inhibited suitably. The bonding strength (S3) is more preferably 15 MPa or more, and particularly preferably 20 MPa or more. The upper limits of the bonding strength is not particularly limited. Preferably the bonding strength is equivalent to the breaking strength of the base material where the first member and the second member are broken.

Examples of the bonding method between the first member and the coupling member, between the second member and the coupling member or between the first member and the second member include methods for bonding the members integrally by bonding with an adhesive agent, by bonding such as deposition or fusion using a thermoplastic resin, by welding, by mechanical bonding such as fastening with a bolt, fastening with a rivet, fitting-in, or caulking, and by molding each member after the other members are disposed in a molding mold when the member is molded. Among those methods, the bonding with an adhesive agent or the mechanical bonding is preferred. In the bonding with an adhesive agent, the adhesive agent has an effect as a seal material in the bonding portion so that liquid such as a cleaning solution for cleaning the imaging stand or blood of an examinee can be prevented from permeating the inside of the imaging table. Thus, the internal mechanism such as the detector can be protected. In the case of the mechanical bonding such as fastening with a bolt, the members can be dismantled easily while the members are bonded firmly. Thus, the maintenance performance of the apparatus can be improved.

In the embodiment of the present invention, the surface opposed to the surface having the opening portion preferably has a thickness of 5 mm or less in orthogonal projection from an X-ray irradiation direction of the imaging table for a mammography apparatus. In the case where the thickness is set at 5 mm or less, the X-ray detector can be disposed up to a position close to a body of an examinee so that even a position close to the body can be imaged. Thus, the region where examination can be performed can be expanded. The thickness in orthogonal projection is more preferably 3 mm or less. On the other hand, the thickness is preferably 1 mm or more in order to inhibit deflection of the imaging table caused by the load applied during imaging.

The material of the coupling member according to the embodiment of the present invention is not particularly limited. However, a metal material or a plastic material excellent in strength and rigidity is preferable because the coupling member couples the body of the mammography apparatus and the imaging table for a mammography apparatus and a load received during the imaging by mammography is applied to the coupling member. The metal material is further preferable.

Examples of the metal material include aluminum, copper, nickel, tin, gold, silver, iron, magnesium, chrome, tungsten, zinc, lead, and alloys of those metals. In addition, the coupling member may be composed of one kind of metal material, or two or more kinds of metals may be combined.

The coupling member in the present intention can be manufactured by a common molding method such as press molding, injection molding, injection compression molding, compression molding, vacuum molding, extrusion molding, sheeting, or casting.

<Mammography Apparatus>

A mammography apparatus according to the embodiment of the present invention is formed by connection of a coupling member, which is bonded to a first member and a second member in an imaging table for a mammography apparatus, to a body of the mammography apparatus.

<Method for Manufacturing Imaging Table>

A method for manufacturing an imaging table according to the embodiment of the present invention is a method for manufacturing an imaging table supported in a cantilever state on an X-ray imaging apparatus. The imaging table includes a planar body including an opening portion to be connected to the apparatus. The planar body includes a first member forming a top surface including an X-ray irradiation surface, a second member forming a bottom surface opposed to the X-ray irradiation surface, and a third member reinforcing the first member. The method for manufacturing an imaging table includes the following steps (I) to (III):

Step (I): a step of heating and pressurizing a preform including a prepreg laminate including continuous fibers (A) and a matrix resin (B) in female and male double-surface molds to thereby mold the first member forming the top surface including the X-ray irradiation surface by a fiber composite material;

Step (II): a step of integrating the second member with at least the first member; and Step (III): a step of integrating the third member with at least the first member.

The application of the imaging table manufactured in the present invention is not limited as long as the imaging table is supported in a cantilever state on an X-ray imaging apparatus. For example, the imaging table is an imaging table for a mammography apparatus.

In a method for manufacturing an imaging table for a mammography apparatus according to the embodiment of the present invention, the imaging table for a mammography apparatus is supported in a cantilever state on the mammography apparatus. The body of the mammography apparatus includes an X-ray generation portion and a pressing plate. The arrangement thereof is exemplified as illustrated in FIG. 1. The imaging table for a mammography apparatus manufactured by the manufacturing method in embodiments of the present invention has an approximately box-like shape with a cavity in its inside. An X-ray detector is often provided inside the cavity. The X-ray detector may be connected to the body of the mammography apparatus directly or may be fixed in the imaging table and connected to the body of the mammography apparatus through wiring. In addition, the X-ray irradiation surface is a flat face region included in the top surface of the imaging table in embodiments of the present invention. The flat face region may be the whole of the top surface of the imaging table or may be a part thereof.

The imaging table for a mammography apparatus manufactured by the manufacturing method according to the embodiment of the present invention includes a first member forming a top surface including an X-ray irradiation surface, and a second member forming a bottom surface opposed to the X-ray irradiation surface. In such a configuration, the number of curved faces or corner portions can be reduced so that an imaging table having a hollow box-like shape can be manufactured with good productivity. In addition, the imaging table in embodiments of the present invention includes a third member separately. Here, the third member is integrated with the first member suffering a load from the pressing plate of the mammography apparatus, so as to reinforce the first member. For example, the third member may be integrated with the second member. The third member is intended to disperse the load applied to the first member or to improve the strength of the imaging table so as to reinforce the first member when the mammography apparatus is used. Preferably the third member is a coupling member via which the obtained imaging table can be connected to the body of the mammography apparatus, in order to reinforce the first member and to make it easy to attach/detach the imaging table to/from the apparatus, thereby enhancing the maintenance performance. The imaging table in the present invention may additionally include a fourth member, a fifth member, and so on.

The method for manufacturing an imaging table for a mammography apparatus in embodiments of the present invention includes a step (I), a step (II) and a step (III). Understandably, the step (I) is not performed after the step (II) and the step (III). However, the other order is not particularly limited. The step (III) may be performed between the step (I) and the step (II), or may be performed simultaneously with the step (I) or the step (II). Alternatively the steps (I), (II) and (III) may be performed simultaneously.

Figure 6:
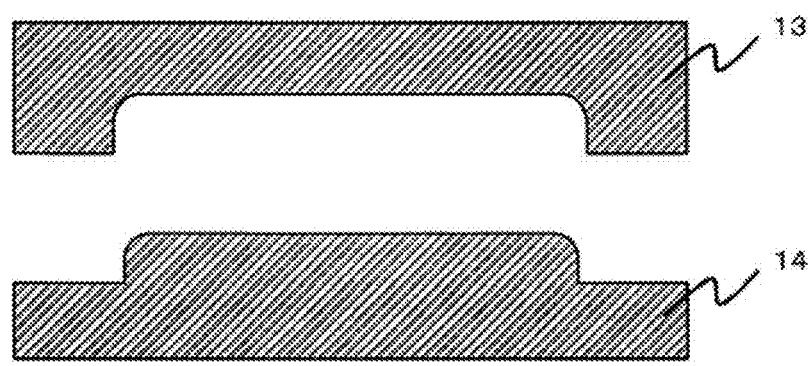
FIG. 6 is a schematic view showing an example of double-surface molds for molding the imaging table for a mammography apparatus according to the embodiment of the present invention.

The step (I) is a step of disposing a preform including a prepreg laminate including continuous fibers (A) and a matrix resin (B) in a pair of female and male double-surface molds shown in FIG. 6, heating and pressurizing the preform by press molding with a pressing machine, thereby obtaining the first member as a fiber composite material. It has been considered that a complicated shape like an imaging table for a mammography apparatus cannot be molded by press molding which involves comparatively high pressure. It has been therefore common sense to perform autoclave molding for such a shape. However, a method for achieving such a shape by press molding by separating the shape into a first member and a second member is found out.

The step (II) is a step of integrating the second member with at least the first member. In the case where the step (III) is performed before the step (II), the step (II) is a step of integrating the second member with both the first member and the coupling member that can be connected to the body of the mammography apparatus. Examples of the integrating method include bonding with an adhesive agent, bonding such as deposition or fusion using a thermoplastic resin, welding, and mechanical bonding such as fastening with a bolt, fastening with a rivet, fitting-in, or caulking. In addition, a method for integrating the second member with the first member and/or the coupling member disposed in a mold directly or through a material composing the second member when the second member is molded is also preferred. In this case, the step (II) and the step (III) are performed simultaneously. In the case where this molding is performed simultaneously with molding of the first member, the steps (I), (II) and (III) are performed simultaneously.

The step (III) is a step of integrating the third member with at least the first member or may be a step of integrating the third member with both the first member and the second member. Example of the integrating method include bonding with an adhesive agent, bonding such as deposition or fusion using a thermoplastic resin, welding, and mechanical bonding such as fastening with a bolt, fastening with a rivet, fitting-in, or caulking. In addition, a method for integrating the third member with the first member and/or the second member disposed in a mold directly or through a material composing the third member when the third member is molded is also preferred.

The position where the third member is integrated is not particularly limited as long as the third member is integrated with the first member. However, the inner wall of the first member is preferable in terms of designability of the obtained imaging table for the mammography apparatus. The inner wall of each of the two side faces in the surface provided with an opening portion, which will be described later, is more preferable. Due to the coupling member bonded to the side face, the X-ray irradiation surface can be expanded so that even a position close to a body of an examinee subjected to mammography can be imaged. Thus, an area which can be examined can be expanded. In order to improve the mechanical characteristic of the integrated region, the position is preferably a position where the third member can be integrated to both the standing wall portion of the first member and the standing wall portion of the second member. In such a configuration, deformation and opening in each side face of the imaging table caused by the load applied during imaging by mammography can be inhibited to improve the positional accuracy during the imaging. Thus, a mammography image can be obtained with high resolution.

<First Member>

The continuous fibers used in the step (I) are not particularly limited. Examples of the continuous fibers include glass fibers, polyacrylonitrile (PAN) based fibers, pitch based carbon fibers (including graphite fibers), and organic fibers such as aramid. Two or more kinds of those fibers may be used in combination. The carbon fibers are preferred in terms of X-ray transparency and high rigidity of the imaging stand. The carbon fibers are not particularly limited, but carbon fibers such as polyacrylonitrile (PAN) based fibers, pitch based carbon fibers, etc. can be used. One kind of those carbon fibers may be used or two or more kinds of them may be used together. Among them, the PAN based carbon fibers are more preferred in terms of balance between strength and elasticity of a molded product obtained therefrom. The strand elastic modulus of the carbon fibers is preferably 200 GPa or more, more preferably 220 GPa or more, and even more preferably 240 GPa or more. In the case where the strand elastic modulus of the carbon fibers is less than 200 GPa, intended properties may not be obtained in the mammography imaging table obtained therefrom.

The matrix resin is not particularly limited, but either a thermosetting resin or a thermoplastic resin may be used. In the case where the matrix resin is a thermosetting resin, the thermosetting resin is cured to serve as the matrix resin due to heating during molding, and, if necessary, due to further heating to a temperature high enough to cure the thermosetting resin after the molding. In the case where the resin is a thermoplastic resin, the resin melted by heating during molding is cooled and solidified to serve as the matrix resin. Examples of the thermosetting resin include epoxy resin, vinyl ester resin, phenolic resin, unsaturated polyester resin, etc. Any thermosetting resin may be used as long as it can cause a crosslinking reaction due to heat to thereby form a three-dimensional crosslinked structure at least partially. On the other hand, a prepreg can be used as a molding base material for forming the first member in the present invention. As a form of the thermosetting resin in the prepreg, the thermosetting resin is preferably in a semi-cured state excellent in tackiness so that the prepreg can be bonded in a pressed manner to another prepreg when the prepreg is laminated. Among the thermosetting resins, an epoxy resin is preferred in consideration of the tackiness in a pasting step and the mechanical characteristic as a molded product obtained therefrom. Preferred examples of the thermoplastic resin include propylene resin, polyethylene resin, polyamide resin, polyester resin, polyarylene sulfide resin, polyphenylene sulfide resin, polyether ketone resin, polyether ether ketone resin, polyether ketone ketone resin, polyether sulfone resin, polyimide resin, polyamide imide resin, polyether imide resin, and polysulfone resin. In addition, a cyclic oligomer which is a precursor of any one of those resins is also used preferably. Among them, a resin excellent in chemical resistance is preferably selected in consideration of cleaning with an antiseptic in the operation of the imaging table for a mammography apparatus.

The prepreg laminate in the step (I) preferably contains a thermosetting resin (A) in terms of tackiness in a lamination step and chemical resistance in a molded product. The thermosetting resin (A) has preferably a cure index of 85% or higher measured by an ion viscometer when the resin is heated at 150° C. for 5 minutes. The cure index is more preferably 90% or higher, and even more preferably 95% or higher. The cure index is an index indicating the degree of curing reaction in the thermosetting resin (A). As the cure index is higher, it becomes easier to release the obtained first member from a molding mechanism, so that the time to heat and cure the thermosetting resin (A) can be shortened. Thus, the heating time in the manufacturing step in which the prepreg containing the thermosetting resin (A) and the continuous fibers is supplied to the molding mechanism can be shortened to improve productivity. The cure index is preferably 100% or less.

A form of the continuous fibers in the prepreg laminate in the step (I) may be a woven fabric form in which a woven texture is formed by continuous fibers, or a form in which continuous fibers are aligned in one direction. In the case of the form in which continuous fibers are aligned in one direction, a molded product obtained therefrom is a unidirectional fiber composite material. In the case of the woven fabric form in which a woven texture is formed by continuous fibers, a molded product obtained therefrom is a woven fabric composite material. Suitably each of those forms may be used alone or in lamination, or the two kinds may be used in lamination. The continuous fibers mean that fibers are set up in a continuous state as a fiber bundle without being cut off into a staple state. Here, the staple designates a short fiber having a length of 100 mm or less.

The unidirectional fiber composite material is composed of layers each including the continuous fibers aligned in one direction, and a matrix resin. The unidirectional fiber composite material may be constituted by a single layer or may be constituted by a laminate in which two or more layers are laminated. In addition, in the case where two or more layers are laminated, the unidirectional fiber composite material may have a configuration in which orientation directions of the continuous fibers are shifted among the layers desirably. Particularly, in terms of isotropy, preferred examples of lamination configurations include a lamination configuration in which each of the orientation directions of the continuous fibers is shifted by 45°, a lamination configuration in which each of the orientation directions of the continuous fibers is shifted by 90°, and a lamination configuration in which each of the orientation directions of the continuous fibers is shifted by 60°.

The woven fabric composite material includes a sheet-like piece in which the continuous fibers are woven, and a matrix resin. The woven fabric composite material typically includes a layer structure, which may be constituted by a single layer or may be constituted by a laminate in which two or more layers are laminated.

The X-ray irradiation surface in the first member in the present invention is preferably formed by a carbon fiber composite material in view of X-ray transparency and high rigidity. Examples of the carbon fiber composite material include a unidirectional carbon fiber composite material including a layer that includes a sheet in which carbon fibers are aligned in one direction, and includes a matrix resin, and include a carbon fiber woven fabric composite material including a layer that includes a sheet in which carbon fibers are woven by a weaving machine, and include a matrix resin. In addition, each of those materials may be constituted by a single layer or may be constituted by a laminate in which two or more layers are laminated. In a more preferred configuration, the carbon fiber composite material is constituted by a laminate in which the unidirectional carbon fiber composite material and the carbon fiber woven fabric composite material are laminated in combination. In such a configuration, it is possible to obtain both the effect of shape followability attributed to the carbon fiber woven fabric composite material and the effect of high rigidity attributed to the unidirectional carbon fiber composite material. For example, a large amount of the unidirectional carbon fiber composite material is used in the top surface of the imaging table contributing to X-ray transparency or rigidity, or in order to make much account to designability, the carbon fiber woven fabric composite material is used in the outermost layer. As the proportion of the carbon fiber woven fabric composite material is increased, shape molding can be achieved more easily. On the other hand, the unidirectional carbon fiber composite material is suitably contained in the X-ray irradiation surface where thickness should be reduced but rigidity should be increased. It is preferable that the proportion of the unidirectional carbon fiber composite material is increased in the X-ray irradiation surface since the aforementioned properties can be improved suitably.

The mammography apparatus has a gentle curved face in terms of designability or has a handle in order to allow an examinee to keep his/her posture during imaging. In the same manner, the imaging table for a mammography apparatus may be also designed to have a gentle curved face excluding the X-ray irradiation surface engaging in mammography imaging or corner portions (parts bent from the X-ray irradiation surface) of the standing wall surface (standing wall surface opposed to the body of the mammography apparatus) to touch the examinee, in order to relax pain of the examinee when the examinee collides with the imaging table.

In a more preferred form, the carbon fiber woven fabric composite material is contained in the outermost layer of the carbon fiber composite material.

In the case where the outermost surface to touch the bare skin of the examinee has such a configuration, the carbon fibers can be prevented from fluffing as compared with the unidirectional carbon fiber composite material even when the resin deteriorates due to a change with time such as exposure to an antiseptic solution in an operating environment. Thus, a stimulus to the examinee can be relaxed. From this point of view, particularly it is preferable that the outermost layer of the X-ray irradiation surface is formed by the carbon fiber woven fabric composite material, and the unidirectional fiber composite material is disposed in inner layers.

Figure 10A:
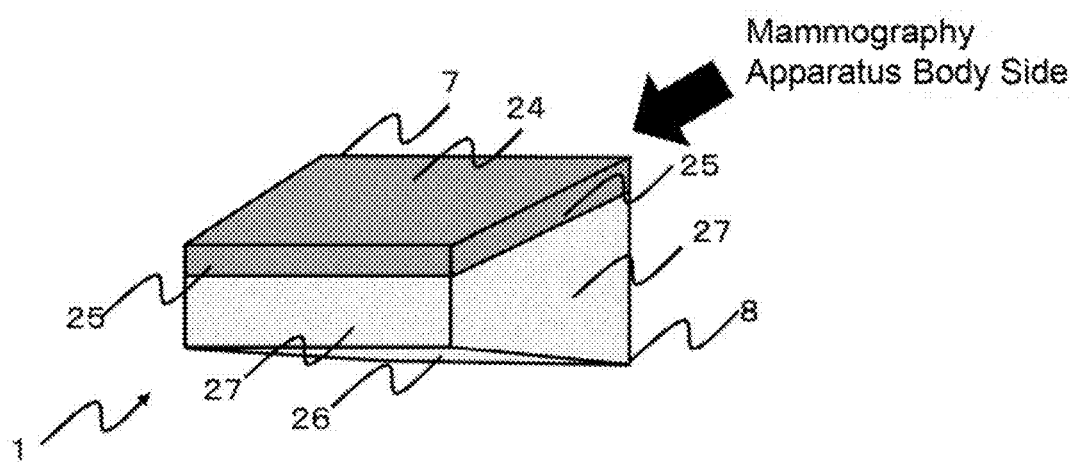
FIG. 10a is a schematic view showing an example of the external appearance of a configuration in which a first member and a second member in the imaging table for a mammography apparatus according to the embodiment of the present invention are integrated.
Figure 10B:
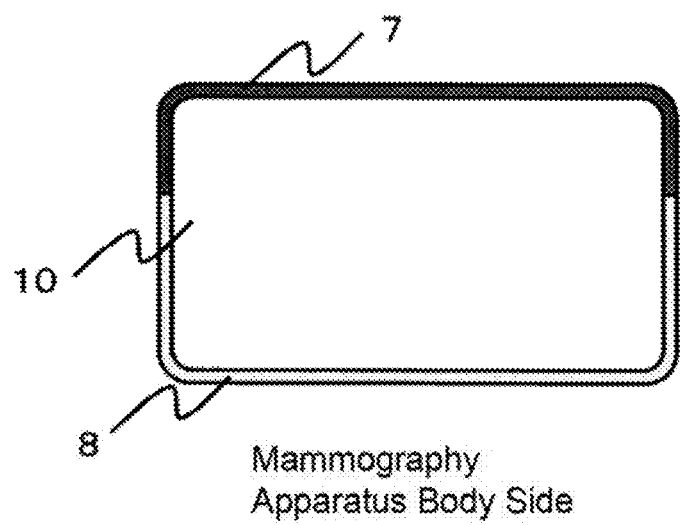
FIG. 10b is a schematic view showing an example of the opening portion of the imaging table for a mammography apparatus according to the embodiment of the present invention.
Figure 10C:
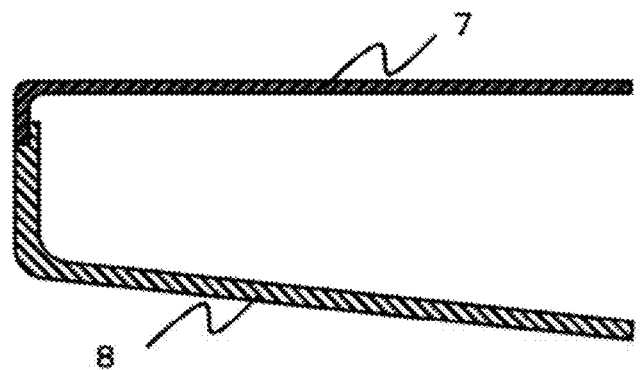
Figure 11A:
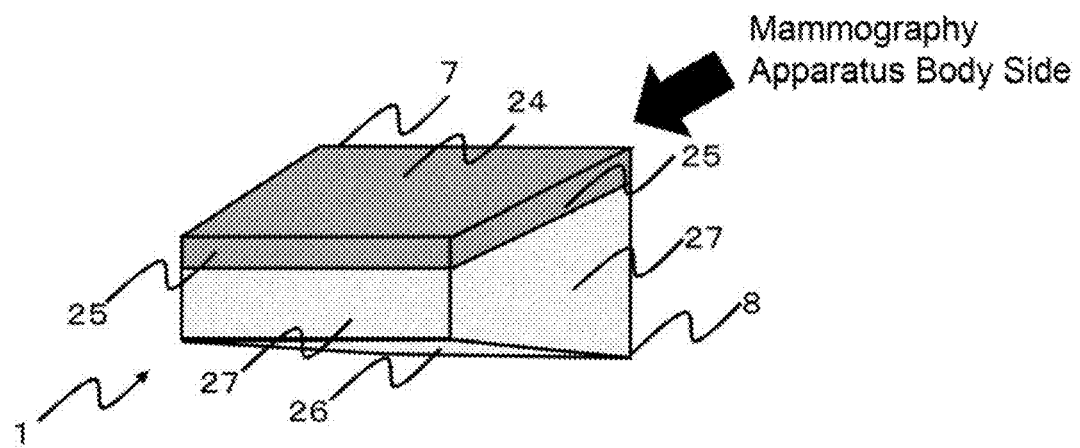
FIG. 11a is a schematic view showing an example of the external appearance of a configuration in which a first member and a second member in the imaging table for a mammography apparatus according to the embodiment of the present invention are integrated.
Figure 11B:
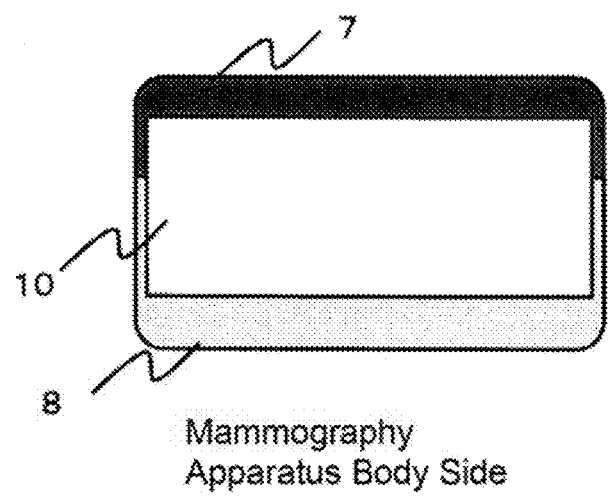
FIG. 11b is a schematic view showing an example of the opening portion of the imaging table for a mammography apparatus according to the embodiment of the present invention.
Figure 11C:
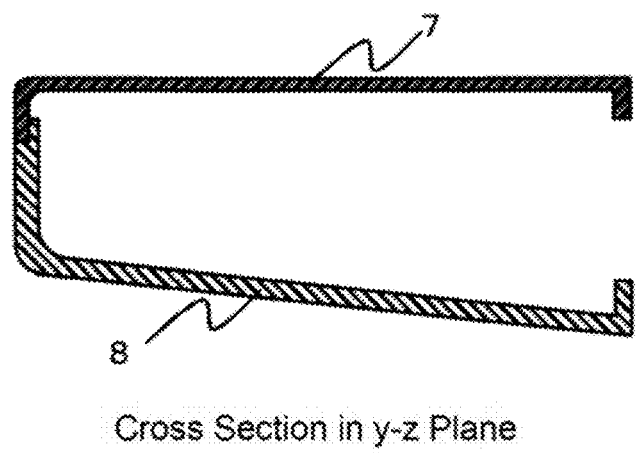

The shape of the first member molded in the step (I) is not particularly limited as long as it can form the top surface including the X-ray irradiation surface. However, it is preferable to form a standing wall erectly provided from the outer circumference of the top surface as shown in FIG. 10*a* and FIG. 11*a*. By virtue of such a structure, deformation caused by a load from the pressing plate during imaging by mammography can be inhibited. The standing wall preferably has a height of 10 mm or more. In the case where the standing wall has a height of 10 mm or more, it is preferably possible to secure a large space where an X-ray detector can be received. The height of the standing wall is a distance between the upper portion of the top surface of the first member and the top end portion of the standing wall. Further, the height of the standing wall is more preferably 20 mm or more, and particularly preferably 30 mm or more. More preferably, a region to be connected to the body of the mammography apparatus is provided so that the imaging table for a mammography apparatus can be detached from and attached to the body of the mammography apparatus easily. Thus, the maintenance performance can be improved suitably. The lateral width of the region to be connected to the body of the mammography apparatus, that is, the size of the opening portion in the horizontal direction when observed from the surface having the opening portion, is preferably 300 mm or more in view of attachability/detachability between the body of the mammography apparatus and the imaging table for a mammography apparatus.

In the imaging stand obtained by the manufacturing method in the present invention, the first member has preferably a specific bending elastic modulus of 2.50 or higher. The specific bending elastic modulus is expressed as $Eb^{1/3} \times \rho^{-1}$ where Eb designates the bending elastic modulus and ρ designates the density. The specific bending elastic modulus is preferably 2.50 or higher because the bending elastic modulus is so high that the first member is less likely to be deformed, and the density is low enough to increase the X-ray transparency. On the other hand, the upper limit of the specific bending elastic modulus is not particularly limited. The specific bending elastic modulus is preferably set at 20.00 or less since the balance between the effect of improving the X-ray transparency and the bending elastic modulus is excellent.

<Second Member>

The second member in the manufacturing method in embodiments of the present invention is another member than the first member. The material of the second member may be the same as the material of the first member. However, it is preferable that the material of the second member is at least one kind selected from a group consisting of metal, plastic and elastomer.

From the viewpoint of processability and dimensional accuracy, metal is preferably used. Examples of kinds of the metal include aluminum, copper, nickel, tin, iron, magnesium, chrome, tungsten, zinc, lead, and alloys of those metals. In addition, the second member may be composed of one kind of metal material, or two or more kinds of metals may be combined.

Plastic is preferably used in terms of moldability/processability and manufacturing cost. Thermosetting resin or thermoplastic resin may be used. Examples of the thermosetting resin include epoxy resin, vinyl ester resin, phenolic resin, polyurethane resin, urea resin, melamine resin, etc. Examples of the thermoplastic resin include polypropylene resin, polyethylene resin, polycarbonate resin, polyamide resin, polyester resin, polyarylene sulfide resin, and polyphenylene sulfide resin. In addition, a cyclic oligomer which is a precursor of any one of those resins is also used preferably. In addition, the plastic may contain a filler such as glass fibers in order to enhance the mechanical characteristic. Alternatively, elastomer may be preferably used in order to protect an examinee. Examples of the elastomer include silicone rubber, urethane rubber, thermoplastic elastomer, etc.

The second member in the manufacturing method in the present invention can be manufactured by a common molding method such as press molding, injection molding, injection compression molding, compression molding, vacuum molding, extrusion molding, sheeting, or casting. The shape of the second member is not particularly limited, but it is preferably a shape in which a bottom surface opposed to the X-ray irradiation surface of the first member and a standing wall portion erectly provided in the outer circumference of the bottom surface are formed as shown in FIG. 10*a*, FIG. 10*b*, FIG. 10*c*, FIG. 11*a*, FIG. 11*b* and FIG. 11*c*. In such a structure, deformation caused by a load from the pressing plate during imaging by mammography can be inhibited. More preferably, a region to be connected to the body of the mammography apparatus is provided. It is preferable to provide the region to be connected to the body of the mammography apparatus because the imaging table for a mammography apparatus can be detached from and attached to the body of the mammography apparatus easily. Thus, the maintenance performance can be improved suitably. The lateral width of the region which is connected to the body of the mammography apparatus is preferably 300 mm or more in terms of attachability/detachability between the body of the mammography apparatus and the imaging table for a mammography apparatus. In the integration of the first member and the second member (step (II)), a structure including an opening portion to be connected to the body of the mammography apparatus in the imaging table for a mammography apparatus can be formed by the region to be bonded to the body of the mammography apparatus in the first member and the region to be bonded to the body of the mammography apparatus in the second member.

Examples of the structure for connecting the body of the mammography apparatus and the imaging table include a method in which the imaging table is connected to a frame provided in the body of the mammography apparatus via a coupling member of the imaging table provided with the coupling member, and a method in which the imaging table for a mammography apparatus has a frame-like coupling member, and the coupling member is fixed to the mammography apparatus, thereby connecting the imaging table thereto.

The material of the third member in the manufacturing method in the present invention is not particularly limited. In the case where the third member is a coupling member, a metal material or a plastic material excellent in strength and rigidity is preferred considering that the third member couples the body of the mammography apparatus and the imaging table for a mammography apparatus with each other and a load during imaging by mammography is applied to the third member. The metal material is further preferred.

From the viewpoint of processability and dimensional accuracy, metal is preferably used. Examples of kinds of the metal include aluminum, copper, nickel, tin, iron, magnesium, chrome, tungsten, zinc, lead, and alloys of those metals. In addition, the third member may be composed of one kind of metal material, or two or more kinds of metals may be combined.

Plastic is preferably used in terms of moldability/processability and manufacturing cost. Thermosetting resin or thermoplastic resin may be used. Examples of the thermosetting resin include epoxy resin, vinyl ester resin, phenolic resin, polyurethane resin, urea resin, melamine resin, etc. Examples of the thermoplastic resin include polypropylene resin, polyethylene resin, polycarbonate resin, polyamide resin, polyester resin, polyarylene sulfide resin, and polyphenylene sulfide resin. In addition, a cyclic oligomer which is a precursor of any one of those resins is also used preferably. In addition, the plastic may contain a filler such as glass fibers in order to enhance the mechanical characteristic.

The third member in the manufacturing method in the present invention can be manufactured by a common molding method such as press molding, injection molding, injection compression molding, compression molding, vacuum molding, extrusion molding, sheeting, or casting.

The method for manufacturing an imaging table for a mammography apparatus in the present invention preferably performs the steps (I) to (III) simultaneously in order to shorten the whole process as long as the method includes the steps (I) to (III). When the preform including the prepreg laminate including the continuous fibers is disposed between the female and male double-surface molds, the third member is disposed together to be heated and pressurized to perform molding (step (I)) of the first member and integration (step (III)) of the first member and the third member simultaneously. Such a method is preferable because the manufacturing process can be shortened, and the positional accuracy of the third member relative to the first member can be improved.

More preferably, it is preferable to use a method in which the thermoplastic resin constituting the second member is insert-molded in an injection molding mold where the first member molded in the step (I) has been disposed, so as to perform molding of the second member and integration (step (II)) of the first member and the second member simultaneously. In such a manufacturing method, processing steps can be simplified as compared with an integration process using an adhesive agent. In addition, it is preferable that the thermoplastic resin constituting the second member is insert-molded in an injection molding mold where the first member molded in the step (I) and the third member molded separately have been disposed, since the integration (step (II)) of the first member and the second member and the integration (step (III)) of the first member and the third member with the thermoplastic resin constituting the second member can be performed simultaneously so that molding of second member and the process of integration into the imaging table for a mammography apparatus can be performed simultaneously, thereby shortening the manufacturing process. More preferably in order to enhance the bonding strength between the first member and the second member, thermoplastic resin of the same kind as the thermoplastic resin forming the second member is contained in a region of the first member which should be bonded to the second member. In the case where the first member has such a configuration, the thermoplastic resin contained in the first member is melted and integrated during the insert molding, thereby improving the bonding strength. As for the configuration in which thermoplastic resin of the same kind as the thermoplastic resin forming the second member is contained in the first member, a method using a preform in which a film of the thermoplastic resin is further laminated on the region to be bonded to the second member in the prepreg laminate can be used in the step (I) by way of example.

EXAMPLES

Examples will be shown below for further specific description of the present invention. Description will be made in the following text using signs in which alphabets are often attached to signs written on the drawings for the sake of discrimination. However, those alphabets are not shown on the drawings.

[Unidirectional Carbon Fiber Prepreg]

"TORAYCA (registered trademark) PREPREG" P3252S-10 made by TORAY Industries, Inc. was prepared as a unidirectional carbon fiber prepreg.

[Carbon Fiber Woven Fabric Prepreg]

"TORAYCA (registered trademark) PREPREG" F6347B-05P made by TORAY Industries, Inc. was prepared as a carbon fiber woven fabric prepreg.

[Calculation of Specific Bending Elastic Modulus]

Using a test piece cut out and obtained from a flat face portion of an X-ray irradiation surface of a manufactured imaging table for a mammography apparatus, a three-point bending elastic modulus Eb was acquired according to JIS K7074 (1988). In addition, density ρ was acquired according to JIS Z8807 (2012) before the examination of the elastic modulus Eb. A specific bending elastic modulus was calculated from the obtained bending elastic modulus Eb and the obtained density ρ by use of the following formula.

(specific bending elastic modulus)=(bending elastic modulus: $Eb$ [GPa])$^{1/3}$×(density: $\rho$ [g/cm$^3$])$^{-1}$

[Measurement of Aluminum Equivalent]

At each of a total of 10 places set at random within the flat face portion of the X-ray irradiation surface of the obtained imaging table for the mammography apparatus, the dose of X-rays transmitted through the flat face portion was measured by a dosimeter. The X-rays were made incident on the flat face portion in a direction perpendicular to the flat face portion at X-ray irradiation tube with voltages of 60 kV and 20 kV by use of an X-ray irradiation device. Then, an aluminum equivalent was calculated from the obtained transmitted X-ray dose. An X-ray high voltage device for diagnosis KXO-30F made by TOSHIBA Corporation was used as the X-ray irradiation device, and Model No. 2025 Radiation Monitor made by Radical Corporation was used as the dosimeter.

Example 1

Figure 5A:
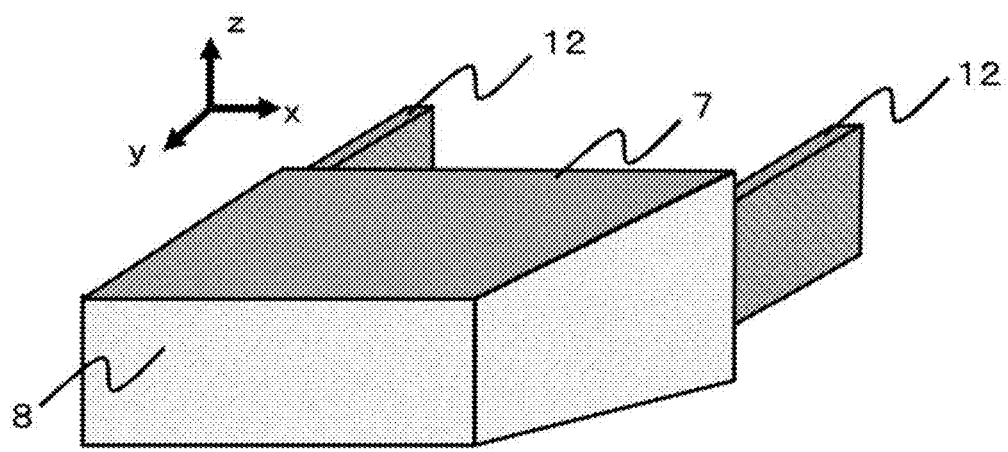
FIG. 5a is a schematic view showing an example of the external appearance of the imaging table for a mammography apparatus according to the embodiment of the present invention.
Figure 5B:
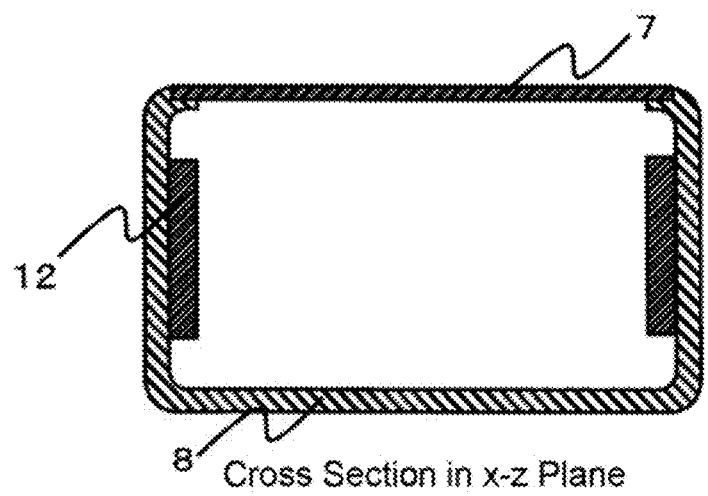
Figure 5C:
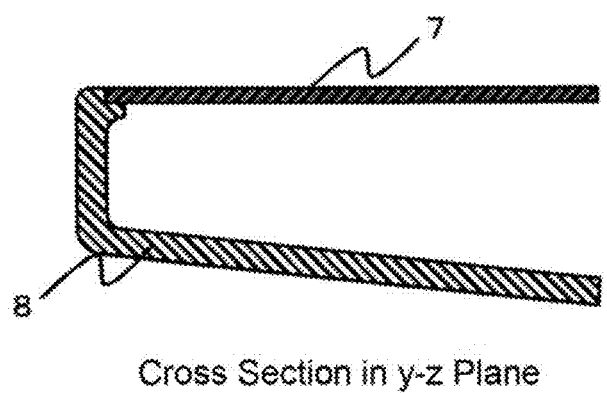

Seven layers of the carbon fiber woven fabric prepreg were laminated to obtain a laminate. The laminate was sandwiched between flat plate-shaped double-surface molds. The laminate was heated and pressurized at a surface pressure of 1.0 MPa at 130° C. for 90 minutes by use of a hydraulic pressing machine to obtain a flat plate-shaped molded product. The molded product was trimmed by a numerical control (NC) router to obtain a first member 7A. Polycarbonate resin pellet ("Panlite (registered trademark)" G-3420 made by Teijin Limited) was used as a raw material to mold a second member 8A having a shape in FIG. 5a by use of an injection molding machine. Sides of the first member 7A are bonded to a standing wall of the second member 8A by use of a two-liquid epoxy adhesive agent to obtain a mammography apparatus imaging table 1A. The mammography apparatus imaging table 1A had an opening portion. Through the opening portion, coupling members 12 made of an aluminum alloy were inserted. By use of the two-liquid epoxy adhesive agent, the coupling members 12 were bonded to inner wall surfaces of two standing wall portions opposed to each other forming the opening portion (FIG. 5a, FIG. 5b and FIG. 5c). The mammography apparatus imaging table 1A was assembled to a mammography apparatus body 2, and a mammography image was taken. The image was obtained without any problem. According to the method described in the aforementioned [Measurement of Aluminum Equivalent], the aluminum equivalent of the X-ray irradiation surface was measured. As a result, the aluminum equivalent was 0.20 mmAL on the condition of the X-ray irradiation tube voltage of 60 kV, and 0.16 mmAL on the condition of 20 kV. In addition, a rectangular test piece was cut out by use of a numerical control (NC) router so that an x-direction of the X-ray irradiation surface of the first member 7A in the obtained mammography apparatus imaging table 1A was set as the longitudinal direction of the test piece. The specific bending elastic modulus of the test piece calculated by the method described in [Calculation of Specific Bending Elastic Modulus Ep] was 2.48.

Example 2

The unidirectional carbon fiber prepreg was laminated with a lamination configuration $[0/90]_{3S}$ to obtain a laminate. Here, [0/90] designates a lamination of two layers in which fiber orientation directions of the unidirectional carbon fiber prepreg were a direction of 0° and a direction of 90° respectively. In addition, the subscript sign 3S designates that the aforementioned lamination of two layers was repeated three times, and the lamination was further performed symmetrically. Accordingly, 12 layers of the unidirectional carbon fiber prepreg were laminated in total.

The laminate was sandwiched between double-surface molds each having a flat plate shape. The laminate was heated and pressurized at a surface pressure of 1.0 MPa at 130° C. for 90 minutes by use of a hydraulic pressing machine to obtain a flat plate-shaped molded product. The molded product was trimmed by a numerical control (NC) router to obtain a first member 7B. The molded product was trimmed so that an x-direction in FIG. 5a coincided with a direction of 0°. Polycarbonate resin pellet ("Panlite (registered trademark)" G-3420 made by Teijin Limited) was used as a raw material to mold a second member 8B having a shape in FIG. 5a, FIG. 5b and FIG. 5c by use of an injection molding machine. Sides of the first member 7B are bonded to a standing wall of the second member 8B by use of a two-liquid epoxy adhesive agent to obtain a mammography apparatus imaging table 1B. The mammography apparatus imaging table 1B had an opening portion. Further, coupling members 12 made of an aluminum alloy were bonded in the same manner (as in Example 1) (FIG. 5a, FIG. 5b and FIG. 5c). The mammography apparatus imaging table 1B was assembled to a mammography apparatus body 2, and a mammography image was taken. The image was obtained without any problem.

According to the method described in the aforementioned [Measurement of Aluminum Equivalent], the aluminum equivalent of the X-ray irradiation surface was measured. As a result, the aluminum equivalent was 0.17 mmAL on the condition of the X-ray irradiation tube voltage of 60 kV, and 0.14 mmAL on the condition of 20 kV. In addition, a rectangular test piece was cut out by use of a numerical control (NC) router so that an x-direction of the X-ray irradiation surface of the first member 7B in the obtained mammography apparatus imaging table 1B was set as the longitudinal direction of the test piece. The specific bending elastic modulus of the test piece calculated by the method described in [Calculation of Specific Bending Elastic Modulus Ep] was 2.71.

Example 3

Seven layers of the carbon fiber woven fabric prepreg were laminated to obtain a laminate. The laminate was disposed between a pair of female and male double-surface molds shown in FIG. 6. The laminate was heated and pressurized at a surface pressure of 1.0 MPa at 130° C. for 90 minutes by use of a hydraulic pressing machine to obtain a molded product. The surface pressure was calculated from an area (projected area viewed from the lamination direction) of the laminate which had not been molded yet. The outer circumference of the molded product was trimmed by a numerical control (NC) router to obtain a first member 7C. A resin sheet having a thickness of 3 mm was produced using ABS resin ("TOYOLAC (registered trademark)" 600-309 made by TORAY Industries, Inc.) by extrusion molding, and the resin sheet was vacuum-molded to obtain a molded product having a standing wall surface. The standing wall surface of the molded product was processed by a numerical control (NC) router to obtain a second member 8C having a step portion in a standing wall end portion. The standing wall of the first member 7C and the standing wall of the second member 8C were bonded by use of a two-liquid epoxy adhesive agent to obtain a mammography apparatus imaging table 1C. The mammography apparatus imaging table 1C had an opening portion. Further, coupling members 12 made of an aluminum alloy were bonded in the same manner (as in Example 1) (FIG. 7a, FIG. 7b and FIG. 7c). The mammography apparatus imaging table 1C was assembled to a mammography apparatus body 2, and a mammography image was taken. The image was obtained without any problem. According to the method described in the aforementioned [Measurement of Aluminum Equivalent], the aluminum equivalent of the X-ray irradiation surface was measured. As a result, the aluminum equivalent was 0.20 mmAL on the condition of the X-ray irradiation tube voltage of 60 kV, and 0.16 mmAL on the condition of 20 kV In addition, a rectangular test piece was cut out by use of a numerical control (NC) router so that an x-direction of the X-ray irradiation surface of the first member 7C in the obtained mammography apparatus imaging table 1C was set as the longitudinal direction of the test piece. The specific bending elastic modulus of the test piece calculated by the method described in [Calculation of Specific Bending Elastic Modulus Ep] was 2.46.

Example 4

A mammography apparatus imaging table 1D including a first member 7D and a second member 8D was obtained in the same method (as in Example 3), except that the unidirectional carbon fiber prepreg was laminated with a lamination configuration [0/90]3s to obtain a laminate, and the obtained laminate was molded with a pair of female and male double-surface molds. The mammography apparatus imaging table 1D had an opening portion. Further, coupling members 12 made of an aluminum alloy were bonded in the same manner (as in Example 1) (FIG. 7a, FIG. 7b and FIG. 7c). The mammography apparatus imaging table 1D was assembled to a mammography apparatus body 2, and a mammography image was taken. The image was obtained without any problem. According to the method described in the aforementioned [Measurement of Aluminum Equivalent], the aluminum equivalent of the X-ray irradiation surface was measured. As a result, the aluminum equivalent was 0.17 mmAL on the condition of the X-ray irradiation tube voltage of 60 kV, and 0.14 mmAL on the condition of 20 kV. In addition, a rectangular test piece was cut out by use of a numerical control (NC) router so that an x-direction of the X-ray irradiation surface of the first member 7D in the obtained mammography apparatus imaging table 1D was set as the longitudinal direction of the test piece. The specific bending elastic modulus of the test piece calculated by the method described in [Calculation of Specific Bending Elastic Modulus Ep] was 2.70.

Example 5

The unidirectional carbon fiber prepreg was laminated with a lamination configuration [0/90/0/90/0/0/90/0/90/0], and the carbon fiber woven fabric prepreg was laminated on one side thereof to obtain a laminate. A mammography apparatus imaging table 1E including a first member 7E and a second member 8E was obtained in the same method (as in Example 3), except that the laminate whose carbon fiber woven fabric prepreg surface was brought into contact with a female mold surface was heated and pressurized by double-surface molds. In addition, the mammography apparatus imaging table 1E had an opening portion. Further, coupling members 12 made of an aluminum alloy were bonded in the same manner (as in Example 1) (FIG. 7a, FIG. 7b and FIG. 7c). The mammography apparatus imaging table 1E was assembled to a mammography apparatus body 2, and a mammography image was taken. The image was obtained without any problem. According to the method described in the aforementioned [Measurement of Aluminum Equivalent], the aluminum equivalent of the X-ray irradiation surface was measured. As a result, the aluminum equivalent was 0.18 mmAL on the condition of the X-ray irradiation tube voltage of 60 kV, and 0.15 mmAL on the condition of 20 kV In addition, a rectangular test piece was cut out by use of a numerical control (NC) router so that an x-direction of the X-ray irradiation surface of the first member 7E in the obtained mammography apparatus imaging table 1E was set as the longitudinal direction of the test piece. The specific bending elastic modulus of the test piece calculated by the method described in [Calculation of Specific Bending Elastic Modulus Ep] was 2.75.

Comparative Example 1

Figure 8:
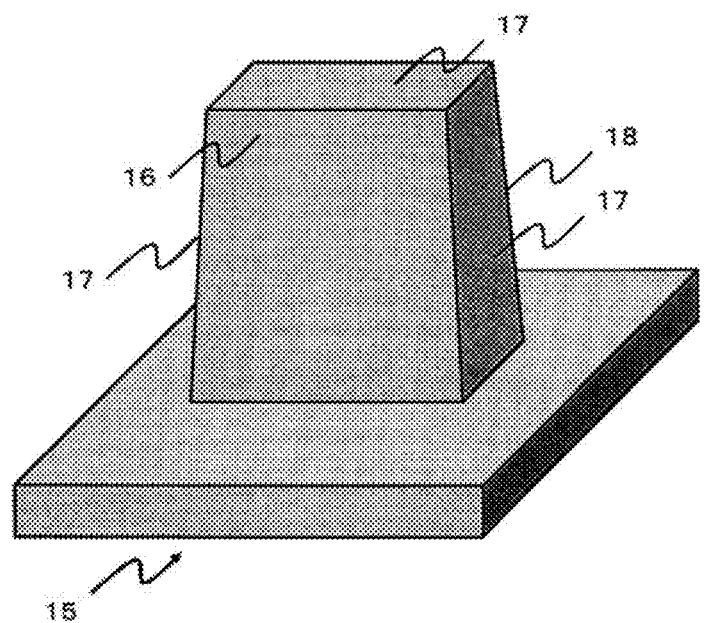
FIG. 8 is a schematic view showing an example of a single-surface mold for molding the imaging table for a mammography apparatus according to the embodiment of the present invention.
Figure 9:
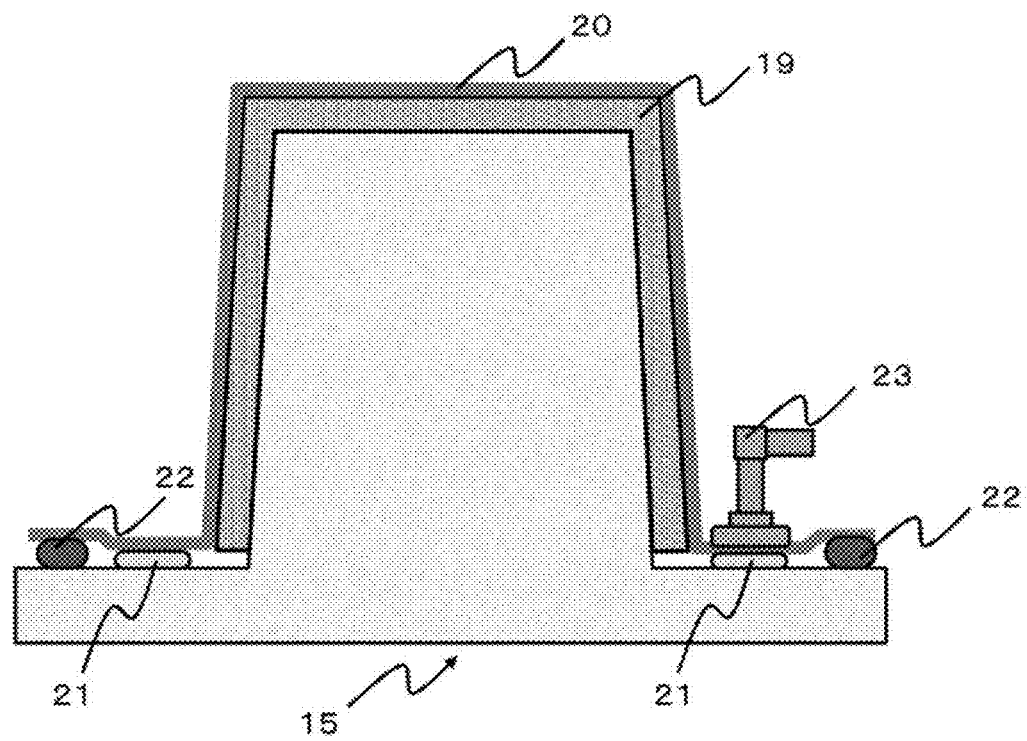
FIG. 9 is a schematic view showing an example of a method for manufacturing an imaging table for a mammography apparatus.

By use of a single-surface mold 15 shown in FIG. 8, the shape of the single-surface mold 15 was imparted from the mold surface to seven layers of the carbon fiber woven fabric prepreg. The single-surface mold 15 includes a surface A 16 for forming an X-ray irradiation surface, a surface B 17 for forming a standing wall of an imaging table for a mammography apparatus, and a surface C 18 for forming a bottom surface of the imaging table for a mammography apparatus. The layers of the carbon fiber woven fabric prepreg were laminated on the surface of the single-surface mold one by one to impart the shape of the single-surface mold 15 to the carbon fiber woven fabric prepreg. In addition, the carbon fiber woven fabric prepreg was cut by three kinds of cutting patterns, that is, a cutting pattern to be laminated on the surface A 16, a cutting pattern to be laminated on the surface B 17, and a cutting pattern to be laminated on the surface C 18. After imparting the shape, the circumference of the single-surface mold 15 was covered with a seal material 22 (tightly closing the mold with a flexible film 20 brought into close contact with the mold) so as to include the region where the carbon fiber woven fabric prepreg had been laminated. After that, a bleeder 21 (playing a roll of a spacer serving as an air passage) made of a thick nonwoven fabric was disposed on an outer circumferential portion of the laminate. A valve 23 provided with a check valve was disposed as a suction opening on the bleeder, and the flexible film 20 were then brought into close contact with the seal material 22 so as to cover the single-surface mold with the flexible film 20. After that, a vacuum pump was connected to the valve 23 serving as a suction opening so as to suck the air from a molding space (a space formed by the single-surface mold 15 and the flexible film 20 and including the region where the carbon fiber woven fabric prepreg had been laminated), thereby reducing the pressure in the molding space. After that, the single-surface mold was thrown into an autoclave apparatus. The temperature was increased at a rate of 2.5° C./min under the condition of 3 atm. After the temperature reached 130° C., the single-surface mold 15 was retained for 90 minutes. By heating and pressurizing the single-surface mold, the thermosetting resin composition in the carbon fiber woven fabric prepreg was cured. After molding, a molded product was released from the single-surface mold 15. End faces of the molded product were trimmed by a numerical control (NC) router to obtain a mammography apparatus imaging table 1F. The mammography apparatus imaging table 1E had an opening portion. Further, coupling members 12 made of an aluminum alloy were bonded in the same manner (as in Example 1). The mammography apparatus imaging table 1F was assembled to a mammography apparatus body 2, and a mammography image was taken. The image was obtained without any problem. According to the method described in the aforementioned [Measurement of Aluminum Equivalent], the aluminum equivalent of the X-ray irradiation surface was measured. As a result, the aluminum equivalent was 0.20 mmAL on the condition of the X-ray irradiation tube voltage of 60 kV, and 0.16 mmAL on the condition of 20 kV. In addition, a rectangular test piece was cut out by use of a numerical control (NC) router so that an x-direction in the obtained mammography apparatus imaging table 1F was set as the longitudinal direction of the test piece. The specific bending elastic modulus of the test piece calculated by the method described in [Calculation of Specific Bending Elastic Modulus Ep] was 2.46.

The characteristics of the imaging stands for the mammography apparatus obtained in the aforementioned Examples and Comparative Examples are listed in Table 1. The mammography apparatus imaging tables 1A and 1C had rigidity and X-ray transparency as high as the mammography apparatus imaging table 1F, and reduced the number of cutting patterns for a base material so that the imaging tables 1A and 1C was able to be manufactured with good productivity. The mammography apparatus imaging table 1B was confirmed to be a mammography apparatus imaging table higher in rigidity and X-ray transparency than the mammography apparatus imaging table 1A. The mammography apparatus imaging table 1D was confirmed to be a mammography apparatus imaging table higher in rigidity and X-ray transparency than the mammography apparatus imaging table 1C. In addition, the surface of each of the mammography apparatus imaging table 1D and the mammography apparatus imaging table 1E was polished with sand paper to expose the carbon fibers. When the surface was traced with a bare hand, fluff of the carbon fibers hitched fingers to give a feeling of pain in the mammography apparatus imaging table 1D. On the other hand, there was no feeling of pain in the mammography apparatus imaging table 1E.

[Measurement of Bonding Strength]

The bonding strength of a bonding portion was measured according to JIS K6850 (1999). To measure the bonding strength (S1) between the first member and the coupling member or the bonding strength (S2) between the second member and the coupling member, materials for forming each bonding structure were prepared, and a test piece obtained by bonding the members in the same method as the bonding structure was produced and measured. In addition, when the bonding structure is based on mechanical bonding, each member to be bonded was prepared in conformity to the standard as to only dimensions thereof, and a test piece in which the members had been bonded by mechanical bonding was produced and measured. In addition, to measure the bonding strength between the first member and the second member, materials for forming each bonding structure were prepared, and a test piece obtained by bonding the members in the same method as the bonding structure was produced and measured. In addition, when the bonding structure is based on mechanical bonding, each member to be bonded was prepared in conformity to the standard as to only dimensions thereof, and a test piece obtained by bonding the members by mechanical bonding was produced and measured.

Example 11

Seven layers of the carbon fiber woven fabric prepreg were laminated to obtain a laminate. The laminate was disposed between a pair of female and male double-surface molds shown in FIG. 6. The laminate was heated and pressurized at a surface pressure of 1.0 MPa at 130° C. for 90 minutes by use of a hydraulic pressing machine to obtain a molded product. The surface pressure was calculated from an area (projected area viewed from the lamination direction) of the laminate before molding. The outer circumference of the molded product was trimmed by a numerical control (NC) router to obtain a first member 7G. Polycarbonate resin pellet ("Panlite (registered trademark)" G-3420 made by Teijin Limited) was used as a raw material to mold a second member 8G having a shape in FIG. 7a, FIG. 7b and FIG. 7c by use of an injection molding machine. Coupling members 12 made of an aluminum alloy were bonded to be laid across the inner wall surface of the standing wall portion of the first member 7G and the inner wall surface of the standing wall portion of the second member 8G by use of a two-liquid urethane adhesive agent (FIG. 7a, FIG. 7b and FIG. 7c) to obtain a mammography apparatus imaging table 1G having the coupling members 12 in the inner wall surfaces of two side surfaces opposed to each other. The mammography apparatus imaging table 1G obtained thus was assembled to a mammography apparatus body, and a mammography image was taken. The obtained image was good. According to the method described in the aforementioned [Measurement of Aluminum Equivalent], the aluminum equivalent of the X-ray irradiation surface was measured. As a result, the aluminum equivalent was 0.20 mmAL on the condition of the X-ray irradiation tube voltage of 60 kV, and 0.16 mmAL on the condition of 20 kV In addition, a rectangular test piece was cut out by use of a numerical control (NC) router so that an x-direction of the X-ray irradiation surface of the first member 7G in the obtained mammography apparatus imaging table 1G was set as the longitudinal direction of the test piece. The specific bending elastic modulus of the test piece calculated by the method described in [Calculation of Specific Bending Elastic Modulus Ep] was 2.46. In addition, the bonding strength measured by the method described in the aforementioned [Measurement of Bonding Strength] is shown in Table 2.

Example 12

A mammography apparatus imaging table 1H was obtained in the same method (as in Example 11), except that each coupling member 12 made of an aluminum alloy was bonded to be laid across the standing wall portion of the first member 7G and the standing wall portion of the second member 8G by use of a two-liquid epoxy adhesive agent. The mammography apparatus imaging table 1H obtained thus was assembled to a mammography apparatus body, and a mammography image was taken. The obtained image was good. According to the method described in the aforementioned [Measurement of Aluminum Equivalent], the aluminum equivalent of the X-ray irradiation surface was measured. As a result, the aluminum equivalent was 0.20 mmAL on the condition of the X-ray irradiation tube voltage of 60 kV, and 0.16 mmAL on the condition of 20 kV. In addition, a rectangular test piece was cut out by use of a numerical control (NC) router so that an x-direction of the X-ray irradiation surface of the first member 7G in the obtained mammography apparatus imaging table 1H was set as the longitudinal direction of the test piece. The specific bending elastic modulus of the test piece calculated by the method described in [Calculation of Specific Bending Elastic Modulus Ep] was 2.46. In addition, the bonding strength measured by the method described in the aforementioned [Measurement of Bonding Strength] is shown in Table 2.

Example 13

The unidirectional carbon fiber prepreg was laminated with a lamination configuration $[0/90]_{3S}$ to obtain a laminate. The laminate was disposed between a pair of female and male double-surface molds shown in FIG. 6. The laminate was heated and pressurized at a surface pressure of 1.0 MPa at 130° C. for 90 minutes by use of a hydraulic pressing machine to obtain a molded product. The surface pressure was calculated from an area (projected area viewed from the lamination direction) of the laminate before molding. The outer circumference of the molded product was trimmed by a numerical control (NC) router to obtain a first member 7I. The other processes were carried out in the same method (as in Example 12) to obtain a mammography apparatus imaging table 1I. The obtained mammography apparatus imaging table 1I was assembled to a mammography apparatus body, and a mammography image was taken. The obtained image was good. According to the method described in the aforementioned [Measurement of Aluminum Equivalent], the aluminum equivalent of the X-ray irradiation surface was measured. As a result, the aluminum equivalent was 0.17 mmAL on the condition of the X-ray irradiation tube voltage of 60 kV, and 0.14 mmAL on the condition of 20 kV. In addition, a rectangular test piece was cut out by use of a numerical control (NC) router so that an x-direction of the X-ray irradiation surface of the first member 7I in the obtained mammography apparatus imaging table 1I was set as the longitudinal direction of the test piece. The specific bending elastic modulus of the test piece calculated by the method described in [Calculation of Specific Bending Elastic Modulus Ep] was 2.70. In addition, the bonding strength measured by the method described in the aforementioned [Measurement of Bonding Strength] is shown in Table 2.

Example 14

Figure 12A:
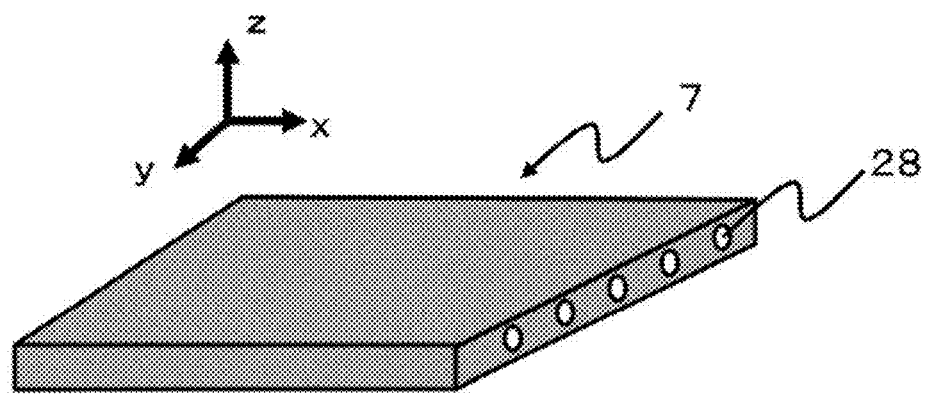
FIG. 12a is a schematic view showing the first member in the imaging table for a mammography apparatus according to the embodiment of the present invention, in which holes for fastening bolts thereto are provided by way of example.
Figure 12B:
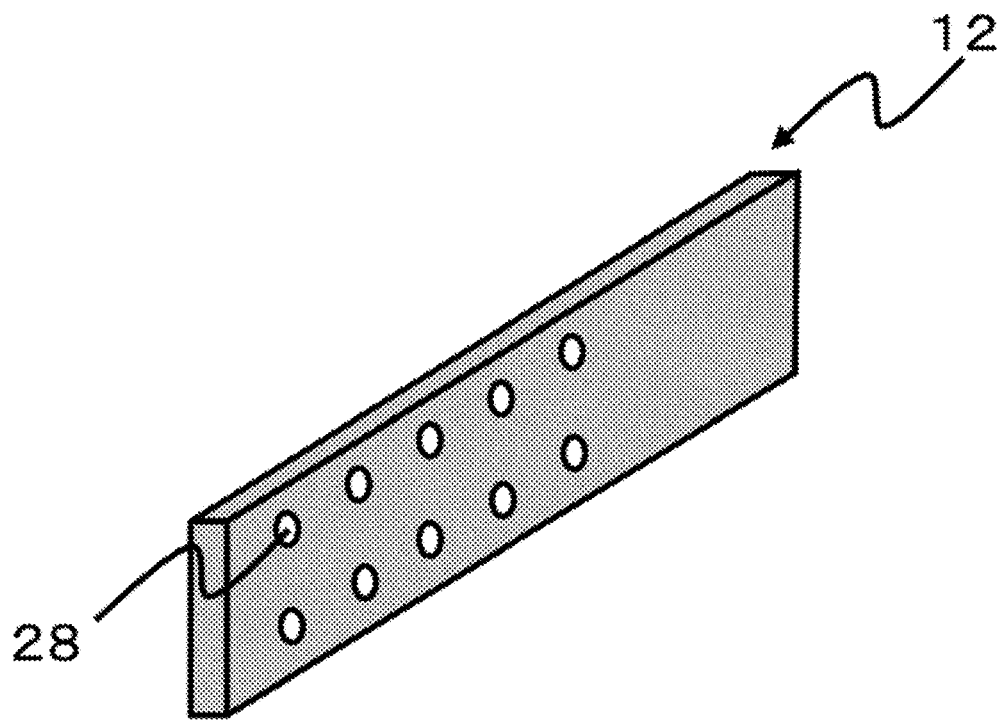
FIG. 12b is a schematic view showing a coupling member in the imaging table for a mammography apparatus according to the embodiment of the present invention, in which holes for fastening bolts thereto are provided by way of example.
Figure 12C:
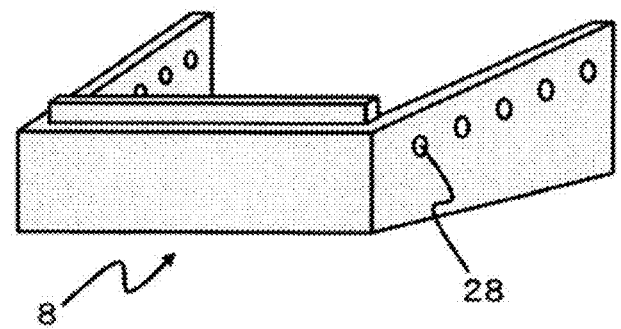
FIG. 12c is a schematic view showing the second member in the imaging table for a mammography apparatus according to the embodiment of the present invention, in which holes for fastening bolts thereto are provided by way of example.
Figure 13A:
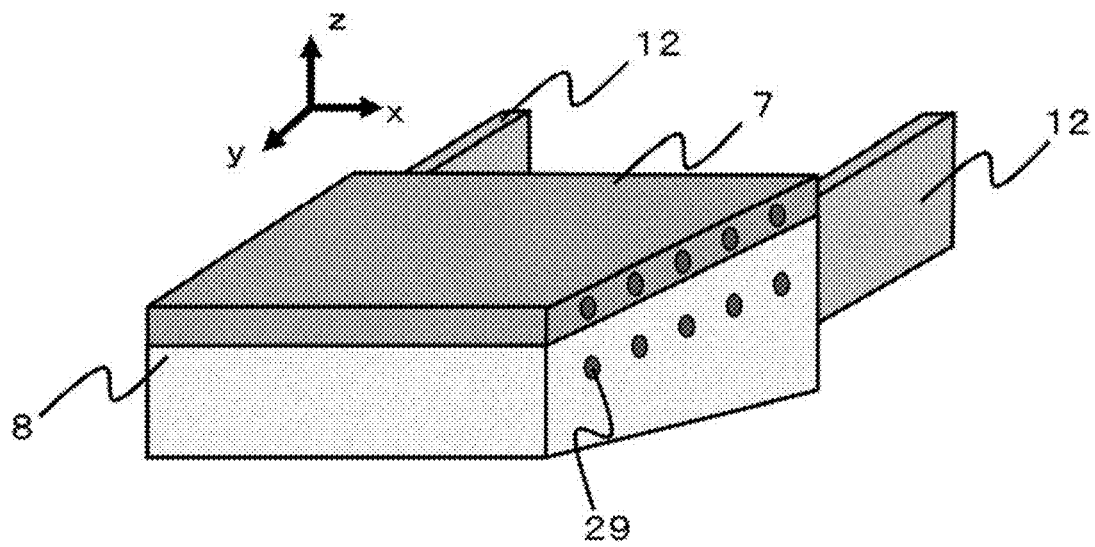
FIG. 13a is a schematic view showing an example of the appearance and sectional shape of the imaging table for a mammography apparatus according to the embodiment of the present invention.
Figure 13B:
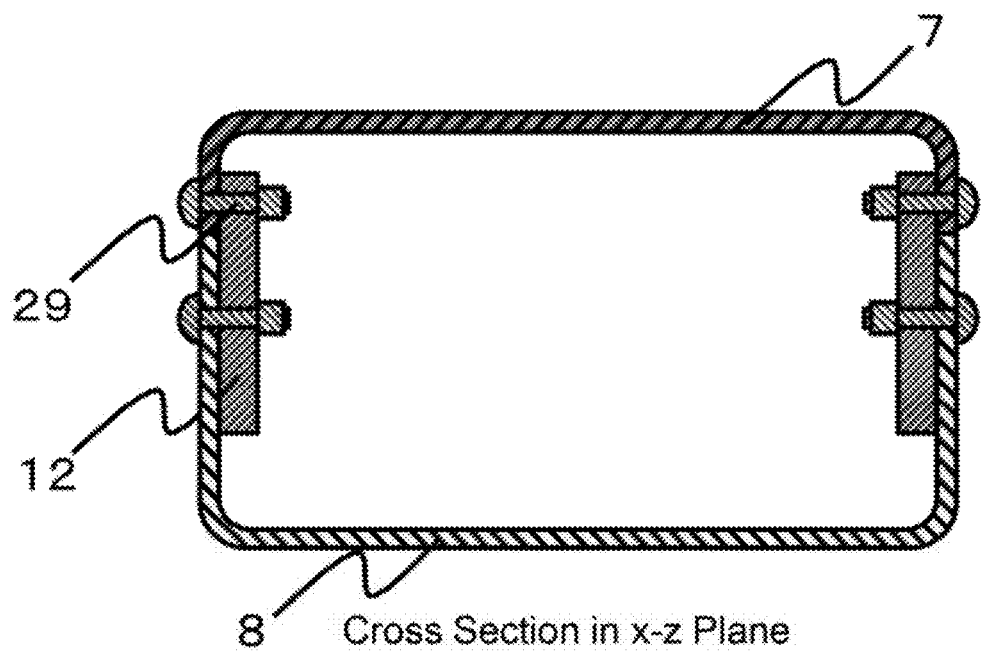
Figure 13C:
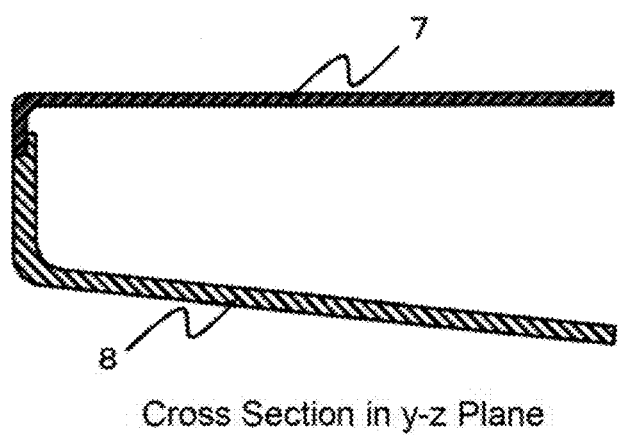

A first member 7J and a second member 8J were obtained in the same method (as in Example 13). The first member 7J and the second member 8J obtained thus were processed by use of a numerical control (NC) router to form bolt fastening holes 28 shown in FIG. 12a, FIG. 12b and FIG. 12c. In addition, each coupling member 12 made of an aluminum alloy was perforated in positions corresponding to the fastening holes by use of a drilling machine. The coupling members 12 made of the aluminum alloy were disposed in positions to be laid across the inner wall surface of the standing wall portion of the first member 7J and the inner wall surface of the standing wall portion of the second member 8J, and mechanically fastened by use of bolts and nuts. In addition, regions (bonding regions) (A1) formed in the standing wall portion of the first member 7J and the second member 8J in an opposed surface to a surface having an opening portion so as to be superimposed and bonded to each other were bonded by use of a two-liquid epoxy adhesive agent to obtain a mammography apparatus imaging table 1J having the coupling members 12 in the inner wall surfaces of two side surfaces opposed to each other (FIG. 13a, FIG. 13b and FIG. 13c). The mammography apparatus imaging table 1J obtained thus was assembled to a mammography apparatus body, and a mammography image was taken. The obtained image was good. According to the method described in the aforementioned [Measurement of Aluminum Equivalent], the aluminum equivalent of the X-ray irradiation surface was measured. As a result, the aluminum equivalent was 0.17 mmAL on the condition of the X-ray irradiation tube voltage of 60 kV, and 0.14 mmAL on the condition of 20 kV. In addition, a rectangular test piece was cut out by use of a numerical control (NC) router so that an x-direction of the X-ray irradiation surface of the first member 7J in the obtained mammography apparatus imaging table 1J was set as the longitudinal direction of the test piece. The specific bending elastic modulus of the test piece calculated by the method described in [Calculation of Specific Bending Elastic Modulus Ep] was 2.71. In addition, the bonding strength measured by the method described in the aforementioned [Measurement of Bonding Strength] is shown in Table 2.

Example 15

The unidirectional carbon fiber prepreg was laminated with a lamination configuration [0/90/0/90/0/0/90/0/90/0], and the carbon fiber woven fabric prepreg was laminated on one side thereof to obtain a laminate. The laminate was disposed between double-surface molds shown in FIG. 6 so that the carbon fiber woven fabric prepreg surface was brought into contact with the female mold surface. The laminate was heated and pressurized at a surface pressure of 1.0 MPa at 130° C. for 90 minutes by use of a hydraulic pressing machine to obtain a molded product. The surface pressure was calculated from an area (projected area viewed from the lamination direction) of the laminate before molding. The outer circumference of the molded product was trimmed by a numerical control (NC) router to obtain a first member 7K. A resin sheet having a thickness of 3 mm was produced using ABS resin ("TOYOLAC (registered trademark)" 600-309 made by TORAY Industries, Inc.) by extrusion molding, and the resin sheet was vacuum-molded to obtain a molded product having a standing wall surface. The standing wall surface of the molded product was processed by a numerical control (NC) router to obtain a second member 8K having a step portion in a standing wall end portion. The molded product was bonded to coupling members 12 made of an aluminum alloy to obtain a mammography apparatus imaging table 1K having the coupling members 12 in the inner wall surfaces of two side surfaces opposed to each other, in the same method (as in Example 13), except that the first member 7K and the second member 8K obtained as described above were used. The obtained mammography apparatus imaging table 1K was assembled to a mammography apparatus body, and a mammography image was taken. The obtained image was good. According to the method described in the aforementioned [Measurement of Aluminum Equivalent], the aluminum equivalent of the X-ray irradiation surface was measured. As a result, the aluminum equivalent was 0.18 mmAL on the condition of the X-ray irradiation tube voltage of 60 kV, and 0.15 mmAL on the condition of 20 kV. In addition, a rectangular test piece was cut out by use of a numerical control (NC) router so that an x-direction of the X-ray irradiation surface of the first member 7K in the obtained mammography apparatus imaging table 1K was set as the longitudinal direction of the test piece. The specific bending elastic modulus of the test piece calculated by the method described in [Calculation of Specific Bending Elastic Modulus Ep] was 2.75. In addition, the bonding strength (S3) measured by the method described in the aforementioned [Measurement of Bonding Strength] is shown in Table 2.

Comparative Example 11

By use of a single-surface mold 15 shown in FIG. 8, the shape of the single-surface mold 15 was imparted from the mold surface to seven layers of the carbon fiber woven fabric prepreg. The single-surface mold 15 includes a surface A 16 for forming an X-ray irradiation surface, a surface B 17 for forming a standing wall of an imaging stand for a mammography apparatus, and a surface C 18 for forming a bottom surface of the imaging table for a mammography apparatus. The layers of the carbon fiber woven fabric prepreg were laminated on the surface of the single-surface mold 15 one by one to impart the shape of the single-surface mold 15 to the carbon fiber woven fabric prepreg. In addition, the carbon fiber woven fabric prepreg was cut by three kinds of cutting patterns, that is, a cutting pattern to be laminated on the surface A 16, a cutting pattern to be laminated on the surface B 17, and a cutting pattern to be laminated on the surface C 18. After imparting the shape, the circumference of the single-surface mold 15 was covered with a seal material 22 (tightly closing the mold with a flexible film 20 brought into close contact with the mold) so as to include the region where the carbon fiber woven fabric prepreg had been laminated. After that, a bleeder 21 (playing a roll of a spacer serving as an air passage) made of a thick nonwoven fabric was disposed on an outer circumferential portion of the laminate. A valve 23 provided with a check valve was disposed as a suction opening on the bleeder, and the seal material 22 and the flexible film 20 were then brought into close contact with the single-surface mold so as to cover the single-surface mold with the flexible film 20. After that, a vacuum pump was connected to the valve 23 serving as a suction opening so as to suck the air from a molding space (a space formed by the single-surface mold 15 and the flexible film 20 and including the region where the carbon fiber woven fabric prepreg had been laminated), thereby reducing the pressure in the molding space. After that, the single-surface mold was thrown into an autoclave apparatus. The temperature of the single-surface mold 15 was increased at a rate of 2.5° C./min under the condition of 3 atm. After the temperature reached 130° C., the single-surface mold 15 was retained for 90 minutes. By heating and pressurizing the single-surface mold, the thermosetting resin composition in the carbon fiber woven fabric prepreg was cured. After molding, a molded product was released from the single-surface mold 15. End faces of the molded product were trimmed by a numerical control (NC) router. Coupling members 12 made of an aluminum alloy were inserted from the opening portion between the two standing wall portions opposed to each other, and bonded to the inner wall surfaces of the two side surfaces opposed to each other by use of a two-liquid epoxy adhesive agent, thereby obtaining a mammography apparatus imaging table 1L. The mammography apparatus imaging table 1L obtained thus was assembled to a mammography apparatus body, and a mammography image was taken. The obtained image was good.

According to the method described in the aforementioned [Measurement of Aluminum Equivalent], the aluminum equivalent of the X-ray irradiation surface was measured. As a result, the aluminum equivalent was 0.20 mmAL on the condition of the X-ray irradiation tube voltage of 60 kV, and 0.16 mmAL on the condition of 20 kV. In addition, a rectangular test piece was cut out by use of a numerical control (NC) router so that an x-direction in the obtained mammography apparatus imaging table 1L was set as the longitudinal direction of the test piece. The specific bending elastic modulus of the test piece calculated by the method described in [Calculation of Specific Bending Elastic Modulus Ep] was 2.46.

Example 16

Seven layers of the carbon fiber woven fabric prepreg were laminated to obtain a laminate. The laminate was disposed between flat plate-shaped double-surface molds. The laminate was heated and pressurized at a surface pressure of 1.0 MPa at 130° C. for 90 minutes by use of a hydraulic pressing machine to obtain a flat plate-shaped molded product. The molded product obtained thus was trimmed by a numerical control (NC) router to obtain a first member 7M. Polycarbonate resin pellet ("Panlite (registered trademark)" G-3420 made by Teijin Limited) was used as a raw material to mold a second member 8M having a shape in FIG. 5*a*, FIG. 5*b* and FIG. 5*c* by use of an injection molding machine. The outer circumference of the first member 7M and the standing wall of the second member 8M were bonded to each other by use of a two-liquid urethane adhesive agent. Coupling members 12 made of an aluminum alloy were inserted from the opening portion and bonded to only the inner wall surface of the standing wall portion of the second member 8M to obtain a mammography apparatus imaging table 1M having the coupling members 12 in the inner wall surfaces of two side surfaces opposed to each other. The mammography apparatus imaging table 1M obtained thus was assembled to a mammography apparatus body, and a mammography image was taken. Due to separation in the bonding surface between the first member 7M and the second member 8M, the image could not be obtained. According to the method described in the aforementioned [Measurement of Aluminum Equivalent], the aluminum equivalent of the X-ray irradiation surface was measured. As a result, the aluminum equivalent was 0.20 mmAL on the condition of the X-ray irradiation tube voltage of 60 kV, and 0.16 mmAL on the condition of 20 kV. In addition, a rectangular test piece was cut out by use of a numerical control (NC) router so that an x-direction of the X-ray irradiation surface of the first member 7M in the obtained mammography apparatus imaging table 1M was set as the longitudinal direction of the test piece. The specific bending elastic modulus of the test piece calculated by the method described in [Calculation of Specific Bending Elastic Modulus Ep] was 2.48. In addition, the bonding strength measured by the method described in the aforementioned [Measurement of Bonding Strength] is shown in Table 2.

The characteristics of the imaging tables for the mammography apparatus obtained in the aforementioned Examples and Comparative Examples are listed in Table 2. The mammography apparatus imaging table 1G had rigidity and X-ray transparency as high as the mammography apparatus imaging table 1L, and reduced the number of cutting patterns for a base material so that the imaging table 1G was manufactured with good productivity. The mammography apparatus imaging table 1H was confirmed to inhibit deformation of the standing wall surface caused by a load applied during imaging, as compared with the mammography apparatus imaging table 1G. The mammography apparatus imaging table 1I was confirmed to be a mammography apparatus imaging table higher in rigidity and X-ray transparency than the mammography apparatus imaging table 1G. In addition, the surface of each of the mammography apparatus imaging table 1I and the mammography apparatus imaging table 1K was polished with sand paper to expose the carbon fibers. When the surface was traced with a bare hand, fluff of the carbon fibers hitched fingers to give a feeling of pain in the mammography apparatus imaging table 1I. On the other hand, there was no feeling of pain in the mammography apparatus imaging table 1K.

[Method for Producing Unidirectional Carbon Fiber Prepreg]

A unidirectional carbon fiber prepreg was produced by the following operations (a) to (b).

(a-1) Preparation of Thermosetting Resin Composition 1

By use of a kneader, 40 parts by mass of bisphenol A epoxy resin (product name: "jER (registered trademark)" 828, made by Mitsubishi Chemical Corporation), 30 parts by mass of bisphenol A epoxy resin ("jER (registered trademark)" 1001), and 30 parts by mass of phenolic novolak epoxy resin ("jER (registered trademark)" 154) were kneaded. Next, 4 parts by mass of dicyandiamide (DICY7, made by Mitsubishi Chemical Corporation) as a curing agent, 3 parts by mass of 3-(3,4-dichlorophenyl) 1,1-dimethylurea (DCMU-99, made by Hodogaya Chemical Co., Ltd.) as a curing accelerator, and 2 parts by mass of polyvinyl formal ("Vinylec (registered trademark)" K, made by Chisso Corporation) as a viscosity modifier were kneaded. Thus, a thermosetting resin composition 1 was produced.

(a-2) Preparation of Thermosetting Resin Composition 2

By use of a kneader, 30 parts by mass of bisphenol A epoxy resin (product name: "jER (registered trademark)" 828, made by Mitsubishi Chemical Corporation), 35 parts by mass of bisphenol A epoxy resin ("jER (registered trademark)" 1001), and 35 parts by mass of phenolic novolak epoxy resin ("jER (registered trademark)" 154) were kneaded. Next, 3.7 parts by mass of dicyandiamide (DICY7, made by Mitsubishi Chemical Corporation) as a curing agent, 3 parts by mass of toluene bis-dimethyl urea (OM-ICURE 24, made by PTI Japan Ltd.) as a curing accelerator, and 3 parts by mass of polymethyl methacrylate ("Matsumoto Microsphere (registered trademark)" M, made by Matsumoto Yushi-Seiyaku Co., Ltd.) as a viscosity modifier were kneaded. Thus, a thermosetting resin composition 2 was produced.

(b-1) Preparation of Unidirectional Carbon Fiber Prepreg 1

The thermosetting resin composition 1 produced in (a-1) was applied to release paper by a knife coater to produce two resin films of 26 g/m². Next, the two resin films were laminated on the both surfaces of sheet-like carbon fibers ("TORAYCA (registered trademark) T700S-12K, made by TORAY Industries, Inc.) arrayed in one direction so that mass per unit area was 100 g/m². Thus, the carbon fibers were impregnated with the resin on the conditions of a roller temperature of 110° C. and a roller pressure of 0.25 MPa to produce a unidirectional carbon fiber prepreg 1 having a carbon fiber mass fraction of 67%.

(b-2) Preparation of Unidirectional Carbon Fiber Prepreg 2

A unidirectional carbon fiber prepreg 2 was produced in the same method as in the aforementioned (b-1), except that the thermosetting resin composition 2 produced in (a-2) was Used.

[Method for Producing Carbon Fiber Woven Fabric Prepreg]

A carbon fiber woven fabric prepreg was produced by the following operations (a) to (b).

(a) Preparation of Thermosetting Resin Composition

The thermosetting resin composition 1 and the thermosetting resin composition 2 described in [Method for Producing Unidirectional Carbon Fiber Prepreg] were produced.

(b-1) Production of Carbon Fiber Woven Fabric Prepreg 1

The thermosetting resin composition 1 produced in (a-1) was applied to release paper by a knife coater to produce two resin films of 78 g/m². Next, the two resin films produced thus were laminated on the both surfaces of a carbon fiber woven fabric base material ("TORAYCA (registered trademark) C06347B, made by TORAY Industries, Inc.). Thus, the carbon fiber woven fabric base material was impregnated with the resin on the conditions of a roller temperature of 110° C. and a roller pressure of 0.25 MPa to produce a carbon fiber woven fabric prepreg 1 having a carbon fiber mass fraction of 56%.

(b-2) Production of Carbon Fiber Woven Fabric Prepreg 2

A carbon fiber woven fabric prepreg 2 was produced in the same method as in the aforementioned (b-1), except that the thermosetting resin composition 2 produced in (a-2) was used.

[Cure Index of Thermosetting Resin]

A dielectric measuring device (MDE-10 cure monitor, made by Holometrix-Micromet Inc.) was used as an ion viscometer. An O-ring made of Viton and having an inner diameter of 32 mm and a thickness of 3 mm was placed on a lower surface of a programmable mini-press MP2000 with a TMS 1-inch sensor embedded in the lower surface. The temperature of the press was set to 150° C. A thermosetting resin was poured into the inside of the O-ring, and the press was closed. A time-dependent change in the ion viscosity of the thermosetting resin was tracked. Measurement was performed at frequencies of 10, 100, 1,000, and 10,000 Hz. Using bundled software, logarithms log α of frequency-dependent ion viscosities were obtained. Here, a cure index (%) by heating at 150° C. for 5 minutes was calculated by the following equation.

$$\text{Cure index} = (\log \alpha t - \log \alpha \min)/\log \alpha \max - \log \alpha \min) \times 100$$

αt: ion viscosity after elapse of 5 minutes (unit: Ω·cm)
α min: minimum value of ion viscosity (unit: Ω·cm)
α max: maximum value of ion viscosity (unit: Ω·cm)

The cure index by heating at 150° C. for 5 minutes measured by the aforementioned method was 80% in the thermosetting resin composition 1, and 94% in the thermosetting resin composition 2.

Example 21

The unidirectional carbon fiber prepreg 1 was laminated with a lamination configuration $[0/90]_{3S}$ to obtain a prepreg laminate. The prepreg laminate was disposed between a pair of double-surface molds, that is, a female mold 13 and a male mold 14 shown in FIG. 6. The prepreg laminate was heated and pressurized at a surface pressure of 1.0 MPa at 150° C. for 30 minutes by use of a hydraulic pressing machine to obtain a first member 7N. The surface pressure was calculated from an area (projected area viewed from the lamination direction) of the laminate which had not been molded yet (step (I)). End faces of the first member 7N were trimmed by a numerical control (NC) router. A resin sheet having a thickness of 3 mm was produced using ABS resin ("TOYOLAC (registered trademark)" 600-309 made by TORAY Industries, Inc.) by extrusion molding, and the resin sheet was vacuum-molded to obtain a molded product having a standing wall surface. The standing wall surface of the molded product was processed by a numerical control (NC) router to obtain a second member 8N having a region 11 to be bonded and superimposed in a standing wall portion. The standing wall of the first member and the standing wall of the second member were bonded and integrated by use of a two-liquid epoxy adhesive agent (step (II)). A molded product obtained in the step (II) had an opening portion. Coupling members 12 made of an aluminum alloy were inserted from the opening portion so as to be laid across both the first member and the second member. Using a two-liquid epoxy adhesive agent, the coupling members 12 were bonded and integrated to the inner wall surfaces of the two standing wall portions opposed to each other so as to form the opening portion (step (III)) to obtain a mammography apparatus imaging table 1N shown in FIG. 7a, FIG. 7b and FIG. 7c. The obtained mammography apparatus imaging table 1N was assembled to a mammography apparatus body 2, and a mammography image was taken. The image was obtained without any problem. According to the method described in the aforementioned [Measurement of Aluminum Equivalent], the aluminum equivalent of the X-ray irradiation surface was measured. As a result, the aluminum equivalent was 0.17 mmAL on the condition of the X-ray irradiation tube voltage of 60 kV, and 0.14 mmAL on the condition of 20 kV. In addition, a rectangular test piece was cut out by use of a numerical control (NC) router so that an x-direction of the X-ray irradiation surface of the first member in the obtained mammography apparatus imaging table 1N was set as the longitudinal direction of the test piece. The specific bending elastic modulus of the test piece calculated by the method described in [Calculation of Specific Bending Elastic Modulus Ep] was 2.70.

Example 22

The unidirectional carbon fiber prepreg 2 was laminated with a lamination configuration $[0/90]_{3S}$ to obtain a laminate. The laminate was disposed between a pair of double-surface molds, that is, a female mold 13 and a male mold 14 shown in FIG. 6. The laminate was heated and pressurized at a surface pressure of 1.0 MPa at 150° C. for 5 minutes by use of a hydraulic pressing machine to obtain a first member 7O (step (I)). As for the other process, the same method (as in Example 21) was used. Then, a mammography apparatus imaging table 1O was obtained. The obtained mammography apparatus imaging table 1O was assembled to a mammography apparatus body 2, and a mammography image was taken. The image was obtained without any problem. According to the method described in the aforementioned [Measurement of Aluminum Equivalent], the aluminum equivalent of the X-ray irradiation surface was measured. As a result, the aluminum equivalent was 0.17 mmAL on the condition of the X-ray irradiation tube voltage of 60 kV, and 0.14 mmAL on the condition of 20 kV. In addition, a rectangular test piece was cut out by use of a numerical control (NC) router so that an x-direction of the X-ray irradiation surface of the first member 7O in the obtained mammography apparatus imaging table 1O was set as the longitudinal direction of the test piece. The specific bending elastic modulus of the test piece calculated by the method described in [Calculation of Specific Bending Elastic Modulus Ep] was 2.70.

Example 23

The unidirectional carbon fiber prepreg 2 was laminated with a lamination configuration [0/90/0/90/0/0/90/0/90/0], and the carbon fiber woven fabric prepreg 2 was laminated on one side thereof to obtain a laminate. The laminate was disposed between double-surface molds so that the carbon fiber woven fabric prepreg surface was brought into contact with the female mold surface. The laminate was heated and pressurized at a surface pressure of 1.0 MPa at 150° C. for 5 minutes by use of a hydraulic pressing machine to obtain a first member 7P (step (I)). As for the other process, the same method (as in Example 21) was used. Then, a mammography apparatus imaging table 1P was obtained. The obtained mammography apparatus imaging table 1P was assembled to a mammography apparatus body 2, and a mammography image was taken. The image was obtained without any problem. According to the method described in the aforementioned [Measurement of Aluminum Equivalent], the aluminum equivalent of the X-ray irradiation surface was measured. As a result, the aluminum equivalent was 0.18 mmAL on the condition of the X-ray irradiation tube voltage of 60 kV, and 0.15 mmAL on the condition of 20 kV. In addition, a rectangular test piece was cut out by use of a numerical control (NC) router so that an x-direction of the X-ray irradiation surface of the first member 7P in the obtained mammography apparatus imaging table 1P was set as the longitudinal direction of the test piece. The specific bending elastic modulus of the test piece calculated by the method described in [Calculation of Specific Bending Elastic Modulus Ep] was 2.75.

Example 24

Figure 14:
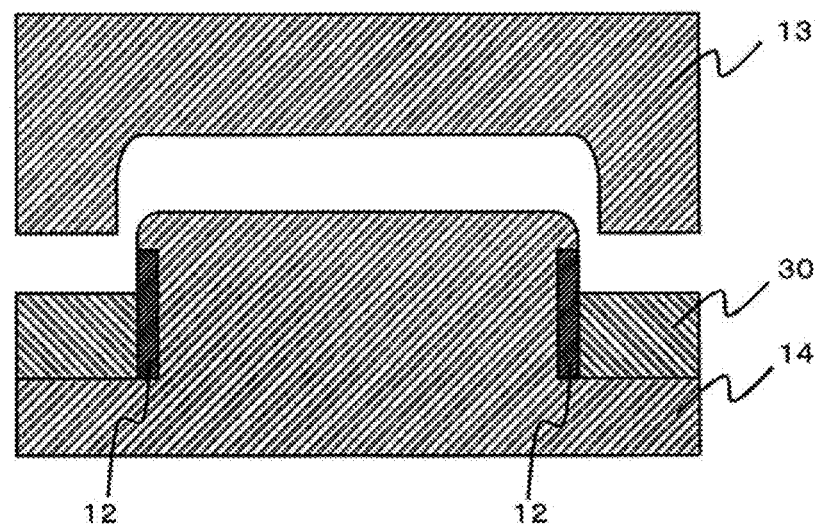
FIG. 14 is a view showing an example of double-surface molds for carrying out a step (I) and a step (II) simultaneously in the method for manufacturing an imaging table for a mammography apparatus according to the embodiment of the present invention.

The unidirectional carbon fiber prepreg 2 was laminated with a lamination configuration [0/90/0/90/0/0/90/0/90/0], and the carbon fiber woven fabric prepreg 2 was laminated on one side thereof to obtain a laminate. The laminate was disposed between a pair of double-surface molds in which coupling members 12 made of an aluminum alloy had been fixed by spacers 30 as shown in FIG. 14, so that the carbon fiber woven fabric prepreg surface was brought into contact with the female mold surface. The laminate was heated and pressurized at a surface pressure of 1.0 MPa at 150° C. for 5 minutes by use of a hydraulic pressing machine to obtain a molded product having a first member 7Q and the coupling members 12 integrated (step (I) and step (II)). End faces of the first member 7Q in the molded product were trimmed by use of a numerical control (NC) router. The molded product obtained thus had a form in which the coupling members 12 were bonded to the inner walls of the standing wall surfaces opposed to each other in the first member 7Q. A resin sheet having a thickness of 3 mm was produced using ABS resin ("TOYOLAC (registered trademark)" 600-309 made by TORAY Industries, Inc.) by extrusion molding, and the resin sheet was vacuum-molded to obtain a molded product having a standing wall surface. The standing wall surface of the molded product was processed by a numerical control (NC) router to obtain a second member 8Q having a bonding region in a standing wall portion. Using a two-liquid epoxy adhesive agent, the molded product in which the first member 7Q and the coupling members 12 had been integrated and the second member 8Q were integrated by bonding between the standing wall of the first member 7Q and the standing wall of the second member 8Q and bonding between the coupling members 12 and the standing wall of the second member (step (II)) to obtain a mammography apparatus imaging table 1Q. The obtained mammography apparatus imaging table 1Q was assembled to a mammography apparatus body 2, and a mammography image was taken. The image was obtained without any problem. According to the method described in the aforementioned [Measurement of Aluminum Equivalent], the aluminum equivalent of the X-ray irradiation surface was measured. As a result, the aluminum equivalent was 0.18 mmAL on the condition of the X-ray irradiation tube voltage of 60 kV, and 0.15 mmAL on the condition of 20 kV. In addition, a rectangular test piece was cut out by use of a numerical control (NC) router so that an x-direction of the X-ray irradiation surface of the first member 7Q in the obtained mammography apparatus imaging table 1Q was set as the longitudinal direction of the test piece. The specific bending elastic modulus of the test piece calculated by the method described in [Calculation of Specific Bending Elastic Modulus Ep] was 2.75.

Example 25

Figure 15:
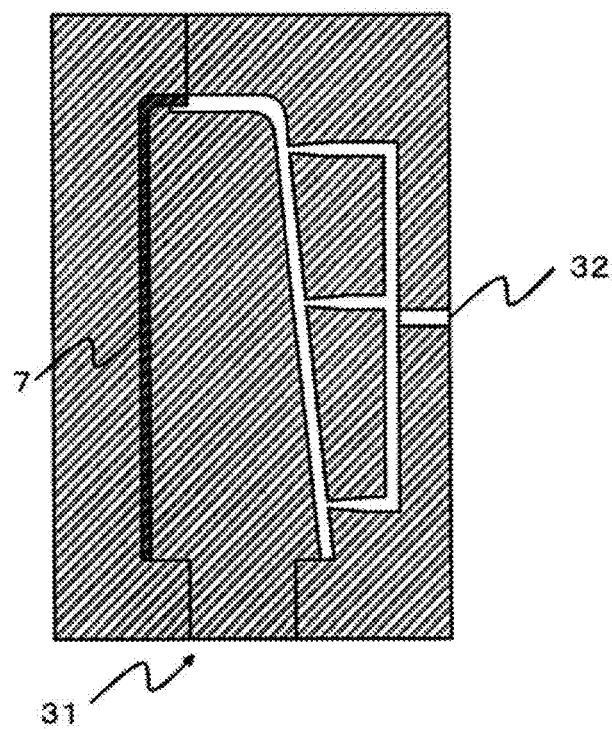
FIG. 15 is a view showing an example of a mold for insert molding in the method for manufacturing an imaging tabled for a mammography apparatus according to the embodiment of the present invention.

The unidirectional carbon fiber prepreg 2 was laminated with a lamination configuration [0/90/0/90/0/0/0/90/0/90/0]. The carbon fiber woven fabric prepreg 2 was laminated on one side thereof, and a polyester nonwoven fabric (100 g/m²) was laminated on the other side of the carbon fiber woven fabric prepreg 2 to obtain a laminate. The laminate was disposed between double-surface molds so that the carbon fiber woven fabric prepreg surface was brought into contact with the female mold surface. The laminate was heated and pressurized at a surface pressure of 1.0 MPa at 150° C. for 5 minutes by use of a hydraulic pressing machine to obtain a first member 7R (step (I)). The first member 7R was disposed in an insert molding mold 31 shown in FIG. 15, and the mold was then clamped. Polycarbonate resin pellet ("Panlite (registered trademark)" G-3420 made by Teijin Limited) was poured into the mold as a raw material by an injection molding machine to form a second member 8R and integrate the first member 7R and the second member 8R (step (II)). An obtained molded product in which the first member 7R and the second member 8R had been integrated had an opening portion. Coupling members 12 made of an aluminum alloy were inserted from the opening portion so as to be laid across both the first member 7R and the second member 8R. Using a two-liquid epoxy adhesive agent, the coupling members 12 were bonded and integrated to the inner wall surfaces of the two standing wall portions opposed to each other so as to form the opening portion (step (III)) to obtain a mammography apparatus imaging table 1R shown in FIG. 7a, FIG. 7b and FIG. 7c. The obtained mammography apparatus imaging table 1R was assembled to a mammography apparatus body 2, and a mammography image was taken. The image was obtained without any problem. According to the method described in the aforementioned [Measurement of Aluminum Equivalent], the aluminum equivalent of the X-ray irradiation surface was measured. As a result, the aluminum equivalent was 0.18 mmAL on the condition of the X-ray irradiation tube voltage of 60 kV, and 0.15 mmAL on the condition of 20 kV In addition, a rectangular test piece was cut out by use of a numerical control (NC) router so that an x-direction of the X-ray irradiation surface of the first member 7R in the obtained mammography apparatus imaging table 1R was set as the longitudinal direction of the test piece. The specific bending elastic modulus of the test piece calculated by the method described in [Calculation of Specific Bending Elastic Modulus Ep] was 2.75.

Comparative Example 21

By use of a single-surface mold 15 shown in FIG. 8, the shape of the single-surface mold 15 was imparted from the mold surface to seven layers of the carbon fiber woven fabric prepreg 1. The single-surface mold 15 includes a surface A 16 for forming an X-ray irradiation surface, a surface B 17 for forming a standing wall of an imaging table for a mammography apparatus, and a surface C 18 for forming a bottom surface of the imaging table for a mammography apparatus. The layers of the carbon fiber woven fabric prepreg 1 were laminated on the surface of the single-surface mold one by one to impart the shape of the single-surface mold 15 to the carbon fiber woven fabric prepreg 1. In addition, the carbon fiber woven fabric prepreg 1 was cut by three kinds of cutting patterns, that is, a cutting pattern to be laminated on the surface A 16, a cutting pattern to be laminated on the surface B 17, and a cutting pattern to be laminated on the surface C 18. After imparting the shape, the circumference of the single-surface mold 15 was covered with a seal material 22 (tightly closing the mold with a flexible film 20 brought into close contact with the mold) so as to include the region where the carbon fiber woven fabric prepreg 1 had been laminated. After that, a bleeder 21 (playing a roll of a spacer serving as an air passage) made of a thick nonwoven fabric was disposed on an outer circumferential portion of the laminate. A valve 23 provided with a check valve was disposed as a suction opening on the bleeder, and the seal material 22 and the flexible film 20 were then brought into close contact with the single-surface mold so as to cover the single-surface mold with the flexible film 20. After that, a vacuum pump was connected to the valve 23 serving as a suction opening so as to suck the air from a molding space (a space formed by the single-surface mold 15 and the flexible film 20 and including the region where the carbon fiber woven fabric prepreg 1 had been laminated), thereby reducing the pressure in the molding space. After that, the single-surface mold was thrown into an autoclave apparatus. The temperature of the single-surface mold 15 was increased at a rate of 2.5° C./min under the condition of 3 atm. The single-surface mold 15 was retained at 150° C. for 30 minutes. By heating and pressurizing the single-surface mold in this manner, the thermosetting resin composition in the carbon fiber woven fabric prepreg 1 was cured. After molding, a molded product was released from the single-surface mold 15. End faces of the molded product were trimmed by a numerical control (NC) router to obtain a mammography apparatus imaging table 1S. The obtained mammography apparatus imaging table 1S had an opening portion. Coupling members 12 made of an aluminum alloy were inserted from the opening portion, and bonded to the inner wall surfaces of the two standing wall portions opposed to each other so as to form the opening portion, respectively by use of a two-liquid epoxy adhesive agent. The mammography apparatus imaging table 1S was assembled to a mammography apparatus body 2, and a mammography image was taken. The image was obtained without any problem. According to the method described in the aforementioned [Measurement of Aluminum Equivalent], the aluminum equivalent of the X-ray irradiation surface was measured. As a result, the aluminum equivalent was 0.20 mmAL on the condition of the X-ray irradiation tube voltage of 60 kV, and 0.16 mmAL on the condition of 20 kV. In addition, a rectangular test piece was cut out by use of a numerical control (NC) router so that an x-direction in the obtained mammography apparatus imaging table 1S was set as the longitudinal direction of the test piece. The specific bending elastic modulus of the test piece calculated by the method described in [Calculation of Specific Bending Elastic Modulus Ep] was 2.46.

The characteristics of the imaging tables for the mammography apparatus obtained in the aforementioned Examples and Comparative Examples are listed in Table 3. From a comparison between (Example 21) and (Comparative Example 21), it was confirmed that the manufacturing time of an imaging table for a mammography apparatus was shortened while discards produced by cutting a prepreg which was a base material were reduced. From a comparison between (Example 21) and (Example 22), it was confirmed that the manufacturing time of a first member was shortened. The surface of the first member in each of the mammography apparatus imaging table 1O and the mammography apparatus imaging table 1P was polished with sand paper to expose the carbon fibers. When the surface was traced with a bare hand, fluff of the carbon fibers hitched fingers to give a feeling of pain in the mammography apparatus imaging table 1O. On the other hand, there was no feeling of pain in the mammography apparatus imaging table 1P. From a comparison among (Example 23), (Example 24) and (Example 25), it was confirmed that the manufacturing process of an imaging stand for a mammography apparatus was simplified.

while maintaining functions required for imaging by mammography in the related art. In addition, the mechanical characteristic of a bonding portion is high. Thus, it is possible to provide an imaging table for a mammography apparatus capable of inhibiting the imaging table from bending due to a load applied during imaging by mammography, so as to improve the quality of a taken image.

TABLE 1

|  |  | Example 1 | Example 2 | Example 3 | Example 4 | Example 5 | Comp. Ex. 1 |
|---|---|---|---|---|---|---|---|
| Form of carbon fiber |  | Woven | Unidirectional | Woven | Unidirectional | Unidirectional + woven | Woven |
| Aluminum equivalent of X-ray irradiation surface [mmAL] | 60 kV | 0.20 | 0.17 | 0.20 | 0.17 | 0.18 | 0.20 |
|  | 20 kV | 0.16 | 0.14 | 0.16 | 0.14 | 0.15 | 0.16 |
| Bending elastic modulus of X-ray irradiation surface: Eb [GPa] |  | 49 | 74 | 48 | 73 | 76 | 48 |
| Density of X-ray irradiation surface: $\rho$ [g/cm$^3$] |  | 1.48 | 1.55 | 1.48 | 1.55 | 1.54 | 1.48 |
| Specific bending elastic modulus of X-ray irradiation surface |  | 2.48 | 2.71 | 2.46 | 2.70 | 2.75 | 2.46 |

TABLE 2

|  |  | Example 11 | Example 12 | Example 13 | Example 14 | Example 15 | Comp. Ex. 11 | Example 16 |
|---|---|---|---|---|---|---|---|---|
| Form of carbon fiber |  | Woven | Woven | Unidirectional | Unidirectional | Unidirectional + woven | Woven | Woven |
| Aluminum equivalent of X-ray irradiation surface [mmAL] | 60 kV | 0.20 | 0.20 | 0.17 | 0.17 | 0.18 | 0.20 | 0.20 |
|  | 20 kV | 0.16 | 0.16 | 0.14 | 0.14 | 0.15 | 0.16 | 0.16 |
| Bending elastic modulus of X-ray irradiation surface: Eb [GPa] |  | 48 | 48 | 73 | 73 | 76 | 48 | 49 |
| Density of X-ray irradiation surface: $\rho$ [g/cm$^3$] |  | 1.48 | 1.48 | 1.55 | 1.55 | 1.54 | 1.48 | 1.48 |
| Specific bending elastic modulus of X-ray irradiation surface |  | 2.46 | 2.46 | 2.70 | 2.70 | 2.75 | 2.46 | 2.48 |
| Bonding strength (S1) [MPa] |  | 7 | 15 | 15 | 20 | 15 | — | — |
| Bonding strength (S2) [MPa] |  | 7 | 13 | 13 | 14 | 11 | — | — |
| Bonding strength (S3) [MPa] |  | 9 | 18 | 18 | 18 | 16 | — | 9 |

TABLE 3

|  |  | Example 21 | Example 22 | Example 23 | Example 24 | Example 25 | Comp. Ex. 21 |
|---|---|---|---|---|---|---|---|
| Form of carbon fiber |  | Unidirectional | Unidirectional | Unidirectional + woven | Unidirectional + woven | Unidirectional + woven | Woven |
| Matrix resin |  | Thermosetting resin composition 1 | Thermosetting resin composition 2 | Thermosetting resin composition 2 | Thermosetting resin composition 2 | Thermosetting resin composition 2 | Thermosetting resin composition 1 |
| Aluminum equivalent of X-ray irradiation surface [mmAL] | 60 kV | 0.17 | 0.17 | 0.18 | 0.18 | 0.18 | 0.20 |
|  | 20 kV | 0.14 | 0.14 | 0.15 | 0.15 | 0.15 | 0.16 |
| Bending elastic modulus of X-ray irradiation surface: Eb [GPa] |  | 73 | 73 | 76 | 76 | 76 | 48 |
| Density of X-ray irradiation surface: $\rho$ [g/cm$^3$] |  | 1.55 | 1.55 | 1.54 | 1.54 | 1.54 | 1.48 |
| Specific bending elastic modulus of X-ray irradiation surface |  | 2.70 | 2.70 | 2.75 | 2.75 | 2.75 | 2.46 |

INDUSTRIAL APPLICABILITY

In an imaging table for a mammography apparatus in the present invention, the number of complicated shapes such as corner portions or curved faces can be reduced to simplify processing steps. Thus, it is possible to provide an imaging table for a mammography apparatus with good productivity While the present invention has been described in detail and with reference to specific embodiments thereof, it will be apparent to one skilled in the art that various changes and modifications can be made therein without departing from the spirit and scope thereof. This application is based on Japanese Patent Application No. 2018-055837 filed on Mar. 23, 2018, Japanese Patent Application No. 2018-055838 filed on Mar. 23, 2018, and Japanese Patent Application No. 2018-055839 filed on Mar. 23, 2018, the entire subject matter of which is incorporated herein by reference.

REFERENCE SIGNS LIST 1 mammography apparatus imaging table
2 mammography apparatus body
3 pressing plate
4 X-ray generation portion
5 X-ray irradiation surface
6 bottom surface of mammography apparatus imaging table
7 first member
8 second member
10 opening portion
11 bonding region (A1)
12 coupling member
13 female mold
14 male mold
15 single-surface mold
16 surface A (top surface and X-ray irradiation surface)
17 surface B (side surface)
18 surface C (bottom surface)
19 prepreg laminate
20 flexible film
21 bleeder
22 seal material
23 valve
24 top surface
25 standing wall portion of first member
26 bottom surface
27 standing wall portion of second member
28 bolt fastening hole
29 bolt
30 spacer
31 insert molding mold
32 injection resin injecting port
33 step portion of first member
34 third member

The invention claimed is:

1. An imaging table to be supported in a cantilever state on a mammography apparatus to support a breast of an examinee,
the imaging table comprising a first member forming a top surface including an X-ray irradiation surface and a first standing wall portion provided from an outer circumference of the top surface, a second member forming a bottom surface opposed to the X-ray irradiation surface and a second standing wall portion provided on an outer circumference of the bottom surface, and a coupling member to be connected to a body of the mammography apparatus, wherein:
the second standing wall portion of the second member is bonded to the first standing wall portion of the first member to form a hollow box-like shape;
the coupling member is bonded to both the first standing wall portion of the first member and the second standing wall portion of the second member;
the height of the first standing wall portion of the first member is 20 mm or more; and
the first member is formed of a carbon fiber composite material and has an aluminum-equivalent X-ray transmission dose in a range of 0.5 mmAL or less at any point in the X-ray irradiation surface.

2. The imaging table according to claim 1, wherein the first member has a specific bending elastic modulus of 2.50 or higher:

(specific bending elastic modulus)=(bending elastic modulus: $[GPa])^{1/3} \times$(density $[g/cm^3])^{-1}$.

3. A mammography apparatus comprising the imaging table according to claim 1, wherein the coupling member of the imaging table is connected to a body of the mammography apparatus.

4. The imaging table for a mammography apparatus according to claim 1, wherein the second standing wall portion of the second member includes a region (A1) where the second standing wall portion is superimposed on and bonded to the first standing wall portion of the first member.

5. A method for manufacturing an imaging table to be supported in a cantilever state on a mammography apparatus to support a breast of an examinee, the imaging table including a first member forming a top surface including an X-ray irradiation surface and a first standing wall portion provided from the outer circumference of the top surface, a second member forming a bottom surface opposed to the X-ray irradiation surface and a second standing wall portion provided on an outer circumference of the bottom surface, and a coupling member to be connected to a body of the mammography apparatus, the height of the first standing wall portion is 20 mm or more,
the method for manufacturing an imaging table comprising the following steps (I) to (III):
Step (I): heating and pressurizing a preform including a prepreg laminate including continuous carbon fibers (A) and a matrix resin (B) in female and male double-surface molds, thereby molding the first member formed of a fiber composite material;
Step (II): bonding the second standing wall portion of the second member with the first standing wall portion of the first member to form a hollow box-like shape; and
Step (III): bonding the coupling member with both the first standing wall portion of the first member and the second standing wall portion of the second member.

6. The method for manufacturing an imaging table according to claim 5, wherein the first standing wall portion is formed on the first member in the step (I).

7. The method for manufacturing an imaging table according to claim 5, wherein the second standing wall portion of the second member is integrated with the first standing wall portion of the first member in the step (II).

8. The method for manufacturing an imaging table according to claim 5, wherein the coupling member is disposed inside the female and male double-surface molds so as to mold the first member in the step (I), thereby performing the step (I) and the step (III) simultaneously.

9. The method for manufacturing an imaging table according to claim 5, wherein in a state where the first member is disposed in the molds, the second member is molded by insert injection molding in the step (II), thereby bonding the second member with the first member.

* * * * *